US011921115B2

(12) United States Patent
Linder et al.

(10) Patent No.: US 11,921,115 B2
(45) Date of Patent: Mar. 5, 2024

(54) PROSTATE ANTIGEN STANDARDS AND USES THEREOF

(71) Applicant: OPKO Diagnostics, LLC, Woburn, MA (US)

(72) Inventors: Vincent Linder, Tewksbury, MA (US); Christina Higgins, Southbridge, MA (US); Kim Pettersson, Turku (FI)

(73) Assignee: OPKO Diagnostics, LLC, Woburn, MA (US)

( * ) Notice: Subject to any disclaimer, the term of this patent is extended or adjusted under 35 U.S.C. 154(b) by 0 days.

(21) Appl. No.: 15/081,331

(22) Filed: Mar. 25, 2016

(65) Prior Publication Data

US 2016/0282349 A1 Sep. 29, 2016
US 2017/0370938 A9 Dec. 28, 2017

Related U.S. Application Data

(60) Provisional application No. 62/139,365, filed on Mar. 27, 2015.

(51) Int. Cl.
*G01N 33/574* (2006.01)
*C12N 9/64* (2006.01)

(52) U.S. Cl.
CPC ..... *G01N 33/57434* (2013.01); *C12N 9/6445* (2013.01); *G01N 2333/96455* (2013.01); *G01N 2496/00* (2013.01)

(58) Field of Classification Search
CPC .............................. G01N 33/57434
USPC ........................................ 435/7.23
See application file for complete search history.

(56) References Cited

U.S. PATENT DOCUMENTS

| | | |
|---|---|---|
| 5,516,639 A | 5/1996 | Tindall et al. |
| 5,585,069 A | 12/1996 | Zanzucchi et al. |
| 5,614,372 A | 3/1997 | Lilja et al. |
| 5,638,828 A | 6/1997 | Lauks et al. |
| 5,672,480 A | 9/1997 | Dowell et al. |
| 5,840,501 A | 11/1998 | Allard et al. |
| 5,939,533 A | 8/1999 | Lilja et al. |
| 5,945,289 A | 8/1999 | Lehrer |
| 6,143,509 A | 11/2000 | Dowell et al. |
| 6,176,962 B1 | 1/2001 | Soane et al. |
| 6,186,660 B1 | 2/2001 | Kopf-Sill et al. |
| 6,444,425 B1 | 9/2002 | Reed et al. |
| 6,713,271 B1 | 3/2004 | Feistel |
| 6,929,918 B1 | 8/2005 | Charrier et al. |
| 7,211,397 B2 | 5/2007 | Mikolajczy et al. |
| 7,258,837 B2 | 8/2007 | Yager et al. |
| 7,605,003 B2 | 10/2009 | Chan et al. |
| 7,736,890 B2 | 6/2010 | Babak et al. |
| 7,872,104 B2 | 1/2011 | Pettersson et al. |
| 7,951,529 B2 | 5/2011 | Li et al. |
| 8,030,057 B2 | 10/2011 | Linder et al. |
| 8,173,433 B2 | 5/2012 | Folkman et al. |
| 8,192,931 B2 | 6/2012 | Fradet et al. |
| 8,580,569 B2 | 11/2013 | Linder et al. |
| 8,591,829 B2 | 11/2013 | Taylor et al. |
| 8,663,600 B2 | 3/2014 | Ulmert |
| 8,765,062 B2 | 7/2014 | Linder et al. |
| 8,932,523 B2 | 1/2015 | Linder et al. |
| 9,182,400 B2 | 11/2015 | Mattsson et al. |
| 9,345,782 B2 | 5/2016 | Strand et al. |
| 9,377,463 B2 | 6/2016 | Krek et al. |
| 9,561,506 B2 | 2/2017 | Taylor et al. |
| 9,643,182 B2 | 5/2017 | Linder et al. |
| 9,672,329 B2 | 6/2017 | Vickers et al. |
| 9,682,376 B2 | 6/2017 | Linder et al. |
| 9,770,715 B2 | 9/2017 | Steinmiller et al. |
| 9,827,563 B2 | 11/2017 | Steinmiller et al. |
| 9,827,564 B2 | 11/2017 | Steinmiller et al. |
| 9,878,324 B2 | 1/2018 | Taylor et al. |
| 10,775,369 B2 | 9/2020 | Linder et al. |
| 2002/0076825 A1 | 6/2002 | Cheng et al. |
| 2003/0235816 A1 | 12/2003 | Slawin et al. |
| 2004/0101914 A1* | 5/2004 | Pettersson ............. C07K 16/40 435/7.23 |
| 2004/0115794 A1 | 6/2004 | Brubaker |
| 2005/0118061 A1 | 6/2005 | Mototsu et al. |
| 2005/0272052 A1 | 12/2005 | Shekar et al. |
| 2005/0282199 A1 | 12/2005 | Slawin et al. |
| 2006/0154276 A1 | 7/2006 | Lois et al. |
| 2006/0269971 A1 | 11/2006 | Diamandis |
| 2007/0065954 A1 | 3/2007 | Taya et al. |
| 2007/0099219 A1 | 5/2007 | Teverovskiy et al. |

(Continued)

FOREIGN PATENT DOCUMENTS

CN 102818892 A 12/2002
CN 1973778 A 6/2007

(Continued)

OTHER PUBLICATIONS

Human Prostate-Specific Antigen (PSA) Kit Technical Data Sheet, AlphaLISA Research Reagents (2009).*
The 1988 Stratagene catalog (p. 39).*
Bradley et al (Cancer Res, 2005, 65(10): 4126-4133).*
Steuber et al (Journal of Urology, 2002, 168: 1917-1922).*
Etzioni et al (Nature Reviews, 2003, 3: internet pp. 1-10).*
Mercer (Immunol Ser, 1990, 53: 39-54).*
Ulmert et al (Clin Chem Lab Med, 2012, 50(11): 1993-1998).*
Nurmikko et al (Clin Chem, 2001, 47(8): 1415-1423).*
U.S. Appl. No. 13/785,058, filed Mar. 5, 2013, Vickers et al.
U.S. Appl. No. 15/197,148, filed Jun. 29, 2016.
U.S. Appl. No. 15/197,172, filed Jun. 29, 2016.
U.S. Appl. No. 14/671,355, filed Mar. 27, 2015, Linder et al.
U.S. Appl. No. 15/143,329, filed Apr. 29, 2016, Dong et al.

(Continued)

*Primary Examiner* — Sean E Aeder
(74) *Attorney, Agent, or Firm* — Wolf, Greenfield & Sacks, P.C.

(57) ABSTRACT

Aspects of the disclosure relate to improved methods for predicting whether a prostate tissue biopsy obtained from a subject will contain detectable prostate cancer. In some embodiments, the disclosure provides improved prostate antigen standards for quantifying levels of prostate antigens.

36 Claims, 2 Drawing Sheets

Specification includes a Sequence Listing.

(56) References Cited

U.S. PATENT DOCUMENTS

| | | |
|---|---|---|
| 2008/0280285 A1 | 11/2008 | Chen et al. |
| 2009/0035773 A1 | 2/2009 | Harvey et al. |
| 2009/0087860 A1 | 4/2009 | Todd et al. |
| 2009/0127454 A1 | 5/2009 | Ritchie et al. |
| 2009/0226912 A1 | 9/2009 | Xu et al. |
| 2010/0100334 A1 | 4/2010 | Otvos |
| 2010/0158756 A1 | 6/2010 | Linder et al. |
| 2010/0168621 A1 | 7/2010 | Neville |
| 2011/0039284 A1 | 2/2011 | Breit et al. |
| 2011/0229489 A1 | 9/2011 | Pons et al. |
| 2011/0301863 A1 | 12/2011 | Auribault et al. |
| 2012/0022793 A1 | 1/2012 | Barker et al. |
| 2012/0122243 A1 | 5/2012 | Kamlage et al. |
| 2012/0141376 A1 | 6/2012 | Einstein et al. |
| 2012/0269701 A1 | 10/2012 | Linder et al. |
| 2013/0157286 A1 | 6/2013 | Linder et al. |
| 2013/0224209 A1 | 8/2013 | Wang et al. |
| 2013/0273643 A1 | 10/2013 | Vickers et al. |
| 2014/0011861 A1 | 1/2014 | McClelland et al. |
| 2014/0023565 A1 | 1/2014 | Taylor et al. |
| 2014/0037716 A1 | 2/2014 | Nowill |
| 2014/0038166 A1 | 2/2014 | Linder et al. |
| 2014/0038167 A1 | 2/2014 | Linder et al. |
| 2014/0038838 A1 | 2/2014 | Narain et al. |
| 2014/0107180 A1 | 4/2014 | Macleod et al. |
| 2014/0134603 A1 | 5/2014 | Sia et al. |
| 2014/0227720 A1 | 8/2014 | Wilson et al. |
| 2014/0234180 A1 | 8/2014 | Linder et al. |
| 2015/0044666 A1 | 2/2015 | Jablonski et al. |
| 2015/0086997 A1 | 3/2015 | Linder et al. |
| 2015/0094221 A1 | 4/2015 | Gronberg et al. |
| 2015/0233901 A1 | 8/2015 | Linder et al. |
| 2015/0284804 A1 | 10/2015 | Gronberg et al. |
| 2015/0317431 A1 | 11/2015 | Gronberg et al. |
| 2015/0343443 A1 | 12/2015 | Linder et al. |
| 2016/0025732 A1 | 1/2016 | Linder et al. |
| 2016/0268112 A1 | 9/2016 | Yip et al. |
| 2016/0305878 A1 | 10/2016 | Steinmiller et al. |
| 2016/0305937 A1 | 10/2016 | Steinmiller et al. |
| 2016/0305938 A1 | 10/2016 | Linder et al. |
| 2016/0320394 A1 | 11/2016 | Dong et al. |
| 2016/0369009 A1 | 12/2016 | Timmermand et al. |
| 2017/0089904 A1 | 3/2017 | Dong et al. |
| 2017/0091379 A1 | 3/2017 | Vickers et al. |
| 2017/0091380 A1 | 3/2017 | Vickers et al. |
| 2017/0108501 A1 | 4/2017 | Gronberg |
| 2017/0165661 A1 | 6/2017 | Taylor et al. |
| 2017/0168060 A1 | 6/2017 | Vickers et al. |
| 2017/0239656 A1 | 8/2017 | Linder et al. |
| 2018/0085753 A1 | 3/2018 | Steinmiller et al. |
| 2019/0072555 A1 | 3/2019 | Linder |
| 2021/0208146 A1 | 7/2021 | Okrongly et al. |

FOREIGN PATENT DOCUMENTS

| | | |
|---|---|---|
| CN | 101329343 A | 12/2008 |
| CN | 101377500 A | 3/2009 |
| EP | 0 635 575 A1 | 1/1995 |
| JP | 2009-524008 A | 6/2009 |
| JP | 2009-189695 A | 8/2009 |
| JP | 2010-243406 A | 10/2010 |
| KR | 20110042678 A | 4/2011 |
| TW | 200538734 A | 12/2005 |
| WO | WO 97/06437 A1 | 2/1997 |
| WO | WO 97/39351 A | 10/1997 |
| WO | WO 99/36776 A1 | 7/1999 |
| WO | WO 99/45398 A1 | 9/1999 |
| WO | WO 02/46448 A2 | 6/2002 |
| WO | WO 2003/029427 A2 | 4/2003 |
| WO | WO 03/100425 A1 | 12/2003 |
| WO | WO 2005/056186 A1 | 6/2005 |
| WO | WO 2010/127322 A1 | 11/2010 |
| WO | WO 2011/027308 A1 | 3/2011 |
| WO | WO 2011/027310 A1 | 3/2011 |
| WO | WO 2012/029080 A1 | 3/2012 |
| WO | WO 2012/129408 A2 | 9/2012 |
| WO | WO 2013/012028 A1 | 1/2013 |
| WO | WO 2013/134179 A2 | 9/2013 |
| WO | WO 2013/172779 A2 | 11/2013 |
| WO | WO 2014/079865 A1 | 5/2014 |
| WO | WO 2014/079874 A1 | 5/2014 |

OTHER PUBLICATIONS

U.S. Appl. No. 15/143,345, filed Apr. 29, 2016.
PCT/US2016/024149, Jun. 30, 2016, International Search Report and Written Opinion.
International Search Report and Written Opinion for PCT/US2016/024149 dated Jun. 30, 2016.
[No Author Listed], Genbank Accession No. 93091201, (Jul. 27, 2016).
Becker et al., Sensitive and specific immunodetection of human glandular kallikrein 2 in serum. Clin Chem. Feb. 2000;46(2):198-206.
Benchikh et al., A panel of kallikrein markers can predict outcome of prostate biopsy following clinical work-up: An independent validation study from the European Randomized Study of Prostate Cancer screening, France. BMC Cancer, 10:635 (2010).
Chun et al., Development and external validation of an extended 10-core biopsy nomogram. European Urology, 52:436-445 (2007).
Eriksson et al., Dual-label time-resolved immunofluorometric assay of free and total prostate-specific antigen based on recombinant Fab fragments. Clin Chem. May 2000;46(5):658-66.
Gupta et al., A four-kallikrein panel for the prediction of repeat prostate biopsy: Data from the European Randomized Study of Prostate Cancer Screening in Rotterdam, Netherlands. Br. J. Cancer, 103:708-714 (2010).
Hara et al., Total and free prostate-specific antigen indexes in prostate cancer screening: value and limitation for Japanese populations. Asian J. Androl., 8(4):429-434 (2006).
Khan et al., Clinical utility of proPSA and "benign" PSA when percent free PSA is less than 15%. Urology, 64(6):1160-1164 (2004).
Lee et al., A meta-analysis of the performance characteristics of the free prostate-specific antigen test. Urology, 67(4):762-768 (2006).
Lilja et al., Prostate-specific antigen and prostate cancer: prediction, detection and monitoring. Nat. Rev. Cancer, 8(4):268-278 (2008).
Lilja et al., Prostate-specific antigen in serum occurs predominantly in complex with alpha 1-antichymotrypsin. Clin Chem. Sep. 1991;37(9):1618-25.
Lövgren et al., Enzymatic action of human glandular kallikrein 2 (hK2). Substrate specificity and regulation by Zn2+ and extracellular protease inhibitors. Eur J Biochem. Jun. 1999;262(3):781-9.
Lövgren et al., Production and activation of recombinant hK2 with propeptide mutations resulting in high expression levels. Eur J Biochem. Dec. 1999;266(3):1050-5.
Michielsen et al., Prediction of free PSA, PSA density and PSA density transition zone in the outcome of sextant prostate biopsies in patients with total PSA between 3 and 15 ng/ml. UroOncology, 4(2):71-76 (2004).
Nam et al., Assessing individual risk for prostate cancer. J. Clin. Oncol., 25(24):3582-3588 (2007).
Nam et al., Prospective multi-institutional study evaluating the performance of prostate cancer risk calculators. J. Clin. Oncol., 29(22):2959-2964 (2011).
Nam et al., Variants of the hK2 protein gene (KLK2) are associated with serum hK2 levels and predict the presence of prostate cancer at biopsy. Clin. Cancer Res., 12(21):6452-6458 (2006).
Nurmikko et al., Production and characterization of novel anti-prostate-specific antigen (PSA) monoclonal antibodies that do not detect internally cleaved Lys145-Lys146 inactive PSA. Clin Chem. Oct. 2000;46(10):1610-8.
Parekh et al., External validation of the Prostate Cancer Prevention Trial risk calculator in a screened population. Urology, 68(6):1152-1155 (2006).
Peltola et al., Immunoassay for the discrimination of free prostate-specific antigen (fPSA) forms with internal cleavages at $Lys_{(145)}$ or $Lys_{(146)}$ from fPSA without internal cleavages at $Lys_{(145)}$ or $Lys_{(146)}$.

(56) References Cited

OTHER PUBLICATIONS

J Immunol Methods. Jun. 30, 2011;369(1-2):74-80. doi: 10.1016/j.jim.2011.04.006. Epub Apr. 28, 2011.

Peltola et al., Intact and internally cleaved free prostate-specific antigen in patients with prostate cancer with different pathologic stages and grades. Urology, 77(4):1009.e1-1009.e8 (2011).

Piironen et al., Determination and analysis of antigenic epitopes of prostate specific antigen (PSA) and human glandular kallikrein 2 (hK2) using synthetic peptides and computer modeling. Protein Sci. Feb. 1998;7(2):259-69.

Rajakoski et al., Epitope mapping of human prostate specific antigen and glandular kallikrein expressed in insect cells. Prostate Cancer Prostatic Dis. Sep. 1997;1(1):16-20.

Sokoll et al., A prospective, multicenter, National Cancer Institute Early Detection Research Network study of [-2]proPSA: improving prostate cancer detection and correlating with cancer aggressiveness. Cancer Epidemiol. Biomarkers Prev., 19(5):1193-1200 (2010).

Talvitie, Delfia immunoassays: Guide to Converting ELISA Assays to DELFIA. PerkinElmer Life and Analytical Sciences. Dec. 18, 2006:1-16. Retrieved on Jun. 11, 2015 from http://www.perkinelmer.com/cmsresources/images/man_delfia_elisa_conversion.pdf.

Thompson et al., Assessing prostate cancer risk: results from the prostate cancer prevention trial. J. Natl. Cancer Inst., 98:529-534 (2006).

Ulmert et al., Prostate-specific antigen at or before age 50 as a predictor of advance prostate cancer diagnosed up to 25 years later: A case-control study. BMC Medicine, 6(6):1-8 (2008).

Ulmert et al., Reproducibility and accuracy of measurements of free and total prostate-specific antigen in serum vs plasma after long-term storage at -20 degrees C. Clin. Chem., 52(2):235-239 (2006).

Van Vugt et al., Prediction of prostate cancer in unscreened men: external validation of a risk Calculator. Eur. J. Cancer 47(6):903-909 (2011).

Vickers et al., A four-kallikrein panel predicts prostate cancer in men with recent screening: Data from the European Randomized Study of Prostate Cancer Screening, Rotterdam. Clin. Cancer Res., 16(12):3232-3239 (2010).

Vickers et al., A panel of kallikrein marker predicts prostate cancer in a large, population-based cohort followed for 15 years without screening. Cancer Epidemiol. Biomarkers Prev., 20(2):255-261 (2011).

Vickers et al., A panel of kallikrein markers can reduce unnecessary biopsy for prostate cancer: Data from the European Randomized Study of Prostate Cancer Screening in Göteborg, Sweden. BMC Med., 6:19 (2008).

Vickers et al., Decision curve analysis: a novel method for evaluating prediction models. Med Decis Making. Nov.-Dec. 2006;26(6):565-74.

Vickers et al., Impact of recent screening on predicting the outcome of prostate cancer biopsy in men with elevated PSA: Data from the European Randomized Study of Prostate Cancer Screening in Gothenburg, Sweden. Cancer, 116(11):2612-2620 (2010).

Vickers et al., Reducing unnecessary biopsy during prostate cancer screening using a fourkallikrein panel: An independent replication. J. Clin. Oncol., 28(15):2493-2498 (2010).

Wenske et al., Evaluation of molecular forms of prostate-specific antigen and human kallikrein 2 in predicting biochemical failure after radical prostatectomy. Int J Cancer. Feb. 1, 2009;124(3):659-63. doi: 10.1002/ijc.23983.

[No Author Listed], Genbank Accession No. 93091201. Feb. 23, 2011.

[No Author Listed], Perkin Elmer Application Note. 2002. Last accessed May 15, 2017 from <http://www.perkinelmer.com/CMSResources/Images/46-72946BRO_Oncology.pdf>. 8 pages.

Bryant et al., Predicting high-grade cancer at ten-core prostate biopsy using four kallikrein markers measured in blood in the ProtecT study. J Natl Cancer Inst. Apr. 11, 2015;107(7). pii: djv095. doi: 10.1093/jnci/djv095. Print Jul. 2015. 6 pages.

Carlsson et al., Predictive value of four kallikrein markers for pathologically insignificant compared with aggressive prostate cancer in radical prostatectomy specimens: results from the European randomized study of screening for prostate cancer section Rotterdam. Eur Urol. Nov. 2013;64(5):693-9.

Chmielewski et al., Serum soluble CD36, assessed by a novel monoclonal antibody-based sandwich ELISA, predicts cardiovascular mortality in dialysis patients. Clin Chim Acta. Dec. 14, 2010;411(23-24):2079-82. doi: 10.1016/j.cca.2010.09.009. Epub Sep. 16, 2010.

Hernandez et al., Predicting the outcome of prostate biopsy: comparison of a novel logistic regression-based model, the prostate cancer risk calculator, and prostate-specific antigen level alone. BJU Int. Mar. 2009;103(5):609-14. doi: 10.1111/j.1464-410X.2008.08127.x. Epub Oct. 24, 2008.

Nurmikko et al., Discrimination of prostate cancer from benign disease by plasma measurement of intact, free prostate-specific antigen lacking an internal cleavage site at Lys145-Lys146. Clin Chem. Aug. 2001;47(8):1415-23.

Solovov et al., Estimation Effectiveness of Logistic Regression and Neural Network Analysis in Prostate Cancer Detection. Siberian Journal of Oncology. 2006;17(1):14-17.

Stephan et al., A (-5, -7) ProPSA Based Artificial Neural Network to Detect Prostate Cancer. European Urology. May 2006;50:1014-20.

Väisänen et al., Development of Sensitive Immunoassays for Free and Total Human Glandular Kallikrein 2. Clinical Chemistry. Sep. 2004;50(9):1607-17.

Virtanen et al., Estimation of Prostate Cancer Probability by Logistic Regression: Free and Total Prostate-specific Antigen, Digital Rectal Examination, and Heredity Are Significant Variables. Clinical Chemistry. 1999;45(7):987-94.

Vickers et al., The predictive value of prostate cancer biomarkers depends on age and time to diagnosis: Towards a biologically-based screening strategy. Int. J. Cancer. 2007;1221:2212-7. Epub Jul. 26, 2007.

U.S. Appl. No. 15/443,102, filed Feb. 27, 2017, Vickers et al.

Haese et al., Standardization of Two Immunoassays for Human Glandular Kallikrein 2. Clinical Chemistry. 2003;49(4):601-10.

Extended European Search Report for EP App. No. 17187201.3 dated Jun. 11, 2018.

Azvolinsky, Study Confirms 4Kscore Accurately Predicts High-Grade Prostate Cancer. Cancer Network. Mar. 2, 2015. Last accessed on Jan. 29, 2018 from <http://www.cancernetwork.com/asco-genitourinary-cancers-symposium/study-confirms-4kscore-accurately-predicts-high-grade-prostate-cancer>. 2 pages.

Carter et al., Percentage of free prostate-specific antigen in sera predicts aggressiveness of prostate cancer a decade before diagnosis. Urology. May 1997;49(3):379-84.

Chuah et al., Ultrasensitive electrochemical detection of prostate-specific antigen (PSA) using gold-coated magnetic nanoparticles as 'dispersible electrodes'. Chem. Commun. 2012;48:3503-5. Epub Feb. 17, 2012.

Finlay et al., Development of Monoclonal Antibodies Specific for Human Glandular Kallikrein (hK2): Development of a Dual Antibody Immunoassay for hK2 with Negligible Prostate-Specific Antigen Cross-reactivity. Urology. May 1, 1998;51(5):804-9.

Kaya et al., High-Sensitivity Immunoassay with Surface Plasmon Field-Enhanced Fluorescence Spectroscopy Using a Plastic Sensor Chip: Application to Quantitative Analysis of Total Prostate-Specific Antigen and GalNAcβ1-4GlcNAc-Linked Prostate-Specific Antigen for Prostate Cancer Diagnosis. Anal. Chem. 2015;87(3):1797-803. Epub Dec. 29, 2014.

Lilja et al., Long-Term Prediction of Prostate Cancer up to 25 Years Before diagnosis of Prostate Cancer Using Prostate Kallikreins Measured at Age 44 to 50 Years. Journal of Clinical Oncology. Feb. 1, 2007;25(4):431-6.

Lin et al., PI-06 Late-Breaking Abstract: The 4Kscore Test as a Predictor of High Grade Prostate Cancer on Biopsy. The Journal of Urology. May 18, 2014;191(4S—Supplement):e224.

Mani et al., Ultrasensitive Immunosensor for Cancer Biomarker Proteins Using Gold Nanoparticle Film Electrodes and Multienzyme-Particle Amplification. ACS Nano. 2009;3(3):585-94. Epub Feb. 13, 2009.

(56) References Cited

OTHER PUBLICATIONS

Mathur et al., MP6-04 the 4KScore Test Predicts High-Grade Prostate Cancer on Biopsy with PSA Less Than 4 NG Per Millimeter. The Journal of Urology. May 15, 2014;191(4S—Supplement):e55.

Mitrunen et al., Dual-Label One-Step Immunoassay for Simultaneous Measurement of Free and Total Prostate-Specific Antigen Concentrations and Ratios in Serum. Clin. Chem. 1995;41(8):1115-20.

O'Dowd et al., Analysis of Repeated Biopsy Results Within 1 Year After a Noncancer Diagnosis. Adult Urology. 2000;55(4):553-8.

Oesterling et al., Effect of cystoscopy, prostate biopsy, and transurethral resection of prostate on serum prostate-specific antigen concentration. Urology. Sep. 1993;42(3):276-82.

Parekh et al., A Multi-institutional Prospective Trial in the USA confirms that the 4Kscore Accurately Identifies Men with High-grade Prostate Cancer. European Urology. Sep. 2015;68:464-70.

Peng et al., Electrochemical immunoassay for the prostate specific antigen using ceria mesoporous nanospheres. Microchimica Acta. Oct. 2014;181(13-14):1505-12.

Pettersson et al., Free and complexed prostate-specific antigen (PSA): in vitro stability, epitope map, and development of immunofluorometric assays for specific and sensitive detection of free PSA and PSA-alpha 1-antichymotrypsin complex. Clin Chem. 1995;41(10):1480-8.

Piironen et al., Immunofluorometric assay for sensitive and specific measurement of human prostatic glandular kallikrein (hK2) in serum. Clinical Chemistry. Jul. 1996;42(7):1034-41.

Punnen et al., PD38-03 the 4KScore is Associated with More Advanced Disease at Radical Prostatectomy; Results from a Multi-Institutional Prospective Trial. The Journal of Urology. May 18, 2015;193(4S, Supplement):e825.

Punnen, A multi-institutional prospective trial in the United States to confirm the 4Kscore identification of men with high-grade prostate cancer. 2015 Genitourinary Cancers Symposium. ASCO Meeting Library. Video Recording, Poster, and Abstract. Feb. 26, 2015. Video last accessed on Jan. 29, 2018 from <https://meetinglibrary.asco.org/record/106267/video>.

Seto et al., Development of ultra-high sensitivity bioluminescent enzyme immunoassay for prostate-specific antigen (PSA) using firefly luciferase. Luminescence. 2001;16:285-90. Epub Jul. 31, 2001.

Thaxton et al., Nanoparticle-based bio-barcode assay redefines "undetectable" PSA and biochemical recurrence after radical prostatectomy. PNAS. Nov. 2009;106(44):18437-42.

Väisänen et al., Intact Free Prostate-Specific Antigen and Free and Total Human Glandular Kallikrein 2. Elimination of Assay Interference by Enzymatic Digestion of Antibodies to F(ab')2 Fragments. Anal. Chem. 2006;78(22):7809-15. Epub Oct. 17, 2006.

Vickers et al., A panel of kallikrein markers can reduce unnecessary biopsy for prostate cancer: Data from the European Randomized Study of Prostate Cancer Screening in Göteborg, Sweden. Journal of Urology. Apr. 1, 2008;179(4):719.

Extended European Search Report for EP App. No. 16773820.2 dated Oct. 10, 2018.

Aly et al., Polygenic Risk Score Improves Prostate Cancer Risk Prediction: Results from the Stockholm-1 Cohort Study. European Urology. Jul. 2011;60(1):21-8. Epub Jan. 18, 2011.

Becker et al., Clinical Value of Human Glandular Kallikrein 2 and Free and Total Prostate-Specific Antigen in Serum from a Population of Men with Prostate-Specific Antigen Levels 3.0 ng/mL or Greater. Adult Urology. 2000;55:694-9.

Cybulski et al., A Novel Founder CHEK2 Mutation is Associated with Increased Prostate Cancer Risk. Cancer Research. Apr. 2004;64(8):2677-9.

Cybulski et al., NBS1 Is a Prostate Cancer Susceptibility Gene. Cancer Research. Feb. 2004;64(4):1215-9.

Ewing et al., Germline Mutations in HOXB13 and Prostate-Cancer Risk. The New England Journal of Medicine. Jan. 12, 2012;366:141-9.

Fisher et al., Generation of monoclonal antibodies specific for human kallikrein 2 (hK2) using hK2-expressing tumors. The Prostate. May 2002;51(3):153-65. Epub Apr. 12, 2002.

Heidenreich et al., Guidelines on Prostate Cancer. Part 6: Diagnosis. European Association of Urology. Apr. 2010:14-27.

Henttu et al., cDNA coding for the entire human prostate specific antigen shows high homologies to the human tissue kallikrein genes. Biochemical and Biophysical Research Communications. Apr. 28, 1989;160(2):903-10.

Henttu et al., Prostate-specific Antigen and Human Glandular Kallikrein: Two Kallikreins of the Human Prostate. Annals of Medicine. 1994;26(3):157-64.

Kim et al., Detection of High Grade Prostate Cancer among PLCO Participants Using a Prespecified 4-Kallikrein Marker Panel. J Urol. Apr. 2017;197(4):1041-7.

Lee et al., A Highly Sensitive Porous Silicon (P-Si)-Based Human Kallikrein 2 (hK2) Immunoassay Platform toward Accurate Diagnosis of Prostate Cancer. Sensors. 2015;15;11972-87.

Leinonen et al., Epitope Mapping of Antibodies against Prostate-specific Antigen with Use of Peptide Libraries. Clinical Chemistry. Dec. 2002;48(12):2208-16.

Leinonen et al., Reactivity of anti-PSA monoclonal antibodies with recombinant human kallikrein-2. Tumour Biology. 1999;20(suppl 1):35-7.

Liton et al., Phage display aided improvement of a unique prostate-specific antigen (PSA) antibody unreactive with Lys145-Lys146 internally cleaved forms. J. Immunol. Methods. Jul. 2015;422:72-9.

Magi et al., Contribution of 32 GWAS-Identified Common Variants to Severe Obesity in European Adults Referred for Bariatric Surgery. PLOS One. Aug. 7, 2013;8(8):e70735. 9 pages.

Nahar et al., Among men with low-grade prostate cancer on prostate biopsy, the 4Kscore to predict prostate cancer aggressiveness at prostatectomy. Journal of Clinical Oncology. Jan. 2016;34(2):suppl 65.

Nilsson et al., Antigenic determinants of prostate-specific antigen (PSA) and development of assays specific for different forms of PSA. British Journal of Cancer. 1997;75:789-97.

Punnen et al., A Multi-Institutional Prospective Trial Confirms Noninvasive Blood Test Maintains Predictive Value in African American Men. J Urol. Jun. 2018;199(6):1459-1463. doi: 10.1016/j.juro.2017.11.113. Epub Dec. 6, 2017.

Punnen et al., Among men with low-grade prostate cancer on prostate biopsy, the 4Kscore predicts the presence of more aggressive prostate cancer. EAU 2015. Madrid. Mar. 20-24, 2015. Abstract and Slides. 4 pages.

Punnen et al., The 4Kscore Predicts the Grade and Stage of Prostate Cancer in the Radical Prostatectomy Specimen: Results from a Multi-institutional Prospective Trial. European Urology Focus. Feb. 2015;3(1):94-9. Epub Jan. 6, 2016.

Selander et al., Serum Macrophage Inhibitory Cytokine-1 Concentrations Correlate with the Presence of Prostate Cancer Bone Metastases. Cancer Epidemiol Biomarkers Prev. 2007;16(3):532-7.

Shiiki et al., Association between saliva PSA and serum PSA in conditions with prostate adenocarcinoma. Biomarkers. 2011;16(6):498-503.

Stenman et al., Summary Report of the TD-3 Workshop: Characterization of 83 Antibodies against Prostate-Specific Antigen. Tumor Biology. 1999;20(suppl 1):1-12.

Steuber et al., Comparison of Free and Total Forms of Serum Human Kallikrein 2 and Prostate-Specific Antigen for Prediction of Locally Advanced and Recurrent Prostate Cancer. Clin Chem. Feb. 2007;53(2):233-40.

Tanase et al., Prostate cancer proteomics: Current trends and future perspectives for biomarker discovery. Oncotarget. 2017;8(11):18497-512.

Vickers et al., Prostate-Specific Antigen Velocity for Early Detection of Prostate Cancer: Result from a Large, Representative, Population-based Cohort. European Urology. Nov. 2009;56(5):753-60.

Vickers et al., The relationship between prostate-specific antigen and prostate cancer risk: the Prostate Biopsy Collaborative Group. Clin. Cancer Res. Sep. 2010;16(17):4374-81. Epub Aug. 24, 2010.

(56) References Cited

OTHER PUBLICATIONS

Wang et al., Western Blotting Analysis of Antibodies to Prostate-Specific Antigen: Specificities for Prostate-Specific Antigen and Prostate-Specific Antigen Fragments. Tumour Biology. 1999;20(suppl 1):79-85.

Wiklund et al., Macrophage inhibitory cytokine-1 (MIC-1/GDF15): a new marker of all-cause mortality. Aging Cell. 2010;9(6):1057-64.

Wilson et al., Fifth-Generation Digital Immunoassay for Prostate-Specific Antigen by Single Molecule Array Technology. Clinical Chemistry. 2011;57(12):1712-21.

[No Author Listed], 4Kscore Test. Opko Health, Inc. Dec. 5, 2014. 4 pages.

Armbruster et al., Limit of Blank, Limit of Detection, and Limit of Quantitation. Clin Biochem Rev. Aug. 2008;29:S49-52.

Kim et al., Potential Utility of Novel Biomarkers in Active Surveillance of Low-Risk Prostate Cancer. Biomed Research International. 2015;11 pages.

[No Author Listed], Delfia Research Reagents. Retrieved Dec. 1, 2019, from https://www.perkinelmer.com/lab-solution/resources/docs/BRO_DELFIAResearchReagents.pdf. 24 pages.

Hirama et al., The impact of baseline [-2]proPSA-related indices on the prediction of pathological reclassification at 1 year during active surveillance for low-risk prostate cancer: the Japanese multicenter study cohort. J Cancer Res Clin Oncol. Feb. 2014;140(2):257-63. doi: 10.1007/s00432-013-1566-2. Epub Dec. 19, 2013.

Isharwal et al., ProPSA and diagnostic biopsy tissue DNA content combination improves accuracy to predict need for prostate cancer treatment among men enrolled in an active surveillance program. Urology. Mar. 2011;77(3):763.e1-6. doi: 10.1016/j.urology.2010.07.526. Epub Jan. 8, 2011.

Mitchell et al., Can High-Grade Prostate Cancer (Gleason 8-10) Be Cured With Definitive Local Therapy Without Testosterone Suppression? Five-Year Outcomes Employing Up-Front Prostatectomy in Patients With Clinically Localized, Nonmetastatic Disease. ARS 2015. Apr. 30, 2015;29(4). 3 pages.

Perez-Amodio et al., Effects of the ionic environment, charge, and particle surface chemistry for enhancing a latex homogeneous immunoassay of C-reactive protein. Anal Chem. Jul. 15, 2001;73(14):3417-25.

Soloway et al., Careful selection and close monitoring of low-risk prostate cancer patients on active surveillance minimizes the need for treatment. Eur Urol. Dec. 2010;58(6):831-5. doi: 10.1016/j.eururo.2010.08.027. Epub Aug. 20, 2010.

Helbling et al., Indolent prostate cancer and active surveillance. Cancer World. Jan. 1, 2010;34:15-21.

Xiong, Clinical study of serum PSA and fPSA assayed by CLIA in diagnosing prostate disease. J Lab Med Clin Sci. 2005;2(5):198-9.

Zhao et al., Interfacial recognition of human prostate-specific antigen by immobilized monoclonal antibody: effects of solution conditions and surface chemistry. J R Soc Interface. Oct. 7, 2012;9(75):2457-67. doi: 10.1098/rsif.2012.0148. Epub May 2, 2012.

Office Action for CN Application No. 201810035218.9 dated Apr. 1, 2022.

[No Author Listed], Early diagnosis and screening of prostate cancer. Perkin Elmer. DELFIA. Mar. 2003:4 pages.

Cui et al., Clinical significance of expression of PSA, hK2, PSMA in the peripheral blood of patients with prostate cancer. Chin J Oncol. Aug. 2004;26(8):479-81.

Goluch et al., A microfluidic detection system based upon a surface immobilized biobarcode assay. Biosens Bioelectron. Apr. 15, 2009;24(8):2397-403. doi: 10.1016/j.bios.2008.12.017. Epub Dec. 24, 2008.

Li, Practicing Physicians' Regular Assessment and Guidance Book: Urology. China Med Sci Tech Press. Oct. 2014:6 pages.

Shariat et al., Beyond Prostate-Specific Antigen: New Serologic Biomarkers for Improved Diagnosis and Management of Prostate Cancer. Rev Urol. 2004;6(2):58-72.

Xu et al., Study of PSA, PSMA and hK2 mRNA in peripheral blood of prostate cancer patients and its clinical implications. J Peking Univ Health Sci. Apr. 2004;36(2):164-8.

Zhang et al., Prostatic Cancer. Shijiazhuang: Hebei Science and Technology Publishing House. Jan. 31, 2007:392-4.

Zhang et al., Research Progress of Tumor Markers for Prostatic Carcinoma. Modern Med Health. May 2011;27(19):2933-5.

EP 17187201.3, Jun. 11, 2018, Extended European Search Report.

U.S. Appl. No. 15/081,331, filed Mar. 25, 2016, Linder et al.

U.S. Appl. No. 17/734,211, filed May 2, 2022, Dong et al.

CN 201810035218.9, Apr. 1, 2022, Office Action.

Nordstrom et al., Comparison Between the Four-kallikrein Panel and Prostate Health Index for Predicting Prostate Cancer. Eur Urol. Jul. 2015;68(1):139-46. doi: 10.1016/j.eururo.2014.08.010. Epub Aug. 20, 2014.

* cited by examiner

PROSTATE ANTIGEN STANDARDS AND USES THEREOF

RELATED APPLICATIONS

This application claims priority under 35 U.S.C. § 119(e) to U.S. Provisional Patent Application No. 62/139,365, filed Mar. 27, 2015, and entitled "PROSTATE ANTIGEN STANDARDS AND USES THEREOF," which is incorporated herein by reference.

BACKGROUND OF INVENTION

Elevated blood levels of total prostate-specific antigen (PSA) are associated with prostate-related disorders, including prostate cancer. There is considerable evidence that measuring levels of isoforms of PSA separately, along with measurement of human kallikrein 2 (hK2), leads to improved predictions relating to the presence of prostate cancer in a subject. Generally, assays to measure elevated levels of prostate antigens, such as PSA isoforms and hK2, utilize antigen standard curves to quantify prostate antigen levels.

SUMMARY OF INVENTION

Aspects of the disclosure relate to a recognition that currently used standards for prostate assays require the use of large quantities of prostate antigens, which is not cost-effective. Furthermore, the wide range of concentrations encompassed by standards in currently used assays may lead to imprecise quantification of antigen concentration because the standard ranges are not properly aligned with the quantities of antigen present in typical clinical sample. Accordingly, it has been recognized that there is a need for new standards that are cost-effective and provide increased accuracy of antigen level quantification.

Many assays to quantify prostate antigen levels rely on comparison of detected antigen signal to a set of values obtained from a set of standard antigen concentrations. However, currently used assays are not cost-effective because they require large amounts of prostate antigen standards. For example, some prostate antigen tests rely on standards having a maximum concentration of up to 350 ng/mL of iPSA or up to 22 ng/mL of hK2 per assay. Furthermore, the large prostate antigen range encompassed by currently used antigen standards may lead to inaccurate quantification of prostate antigen levels in a sample and increase the risk of an incorrect diagnosis. The instant disclosure solves these problems by providing cost-effective compositions and methods for improved quantification of prostate antigen levels.

Accordingly, in one aspect, the disclosure provides a method for quantifying levels of a prostate antigen. In some embodiments, the method involves performing an immunoassay to detect presence of a prostate antigen in a sample; and quantifying levels of the prostate antigen detected in the sample in relation to a minimal set of informative prostate antigen standards detected using the same immunoassay. In some embodiments, a minimal set of informative prostate antigen standards comprises at least two titers containing predetermined quantities of prostate antigens, in which the largest titer of the set is between i) the blood prostate antigen concentration of the upper quartile of a target population of subjects and ii) 75-fold higher than that blood prostate antigen concentration. In some embodiments, a quantity of the smallest non-zero titer of the set is below the limit of quantification of the immunoassay. In some embodiments, a target population of subjects consists of men, the median age of which is in a range of 60 to 70 years. In some embodiments, a target population of subjects consists of men, the lower quartile age of which is in a range of 55 to 65 years. In some embodiments, a target population of subjects consists of men, the upper quartile age of which is in a range of 65 to 75 years. In some embodiments, a prostate antigen is selected from the group consisting of: total prostate specific antigen (tPSA), free prostate specific antigen (fPSA), intact prostate specific antigen (iPSA), and human kallikrein 2 (hK2). In some embodiments, a prostate antigen is iPSA or hK2. In some embodiments, a prostate antigen is intact prostate specific antigen (iPSA). In some embodiments, the smallest non-zero titer of the set is 0.025 ng/mL. In some embodiments, the largest titer of the set is 15 ng/mL. In some embodiments, a minimal set of informative prostate antigen standards consists of the following titers of prostate antigen standard: 0 ng/mL, 0.025 ng/mL, 0.089 ng/mL, 0.322 ng/mL, 1.157 ng/mL, 4.167 ng/mL, and 15 ng/mL. In some embodiments, the prostate antigen is hK2. In some embodiments, the smallest non-zero titer of the set is 0.002 ng/mL. In some embodiments, the largest titer of the set is 8 ng/mL. In some embodiments, a minimal set of informative prostate antigen standards consists of the following titers of prostate antigen standard: 0 ng/mL, 0.002 ng/mL, 0.011 ng/mL, 0.055 ng/mL, 0.290 ng/mL, 1.524 ng/mL, and 8 ng/mL. In some embodiments, a minimal set of informative prostate antigen standards consists of seven titers of prostate antigen standard. In some embodiments, each intermediate titer of prostate antigen standard is equidistant from the titer above and below it on a logarithmic scale. In some embodiments, the immunoassay is selected from the group consisting of DELFIA®, Enzyme Linked Immunoassay (ELISA), radioimmunoassay (RIA), sandwich assay, western blot assay, and immunoprecipitation assay (IPA). In some embodiments, the immunoassay is a DELFIA®. In some embodiments, the immunoassay is an ELISA. In some embodiments, a sample is obtained from a human subject. In some embodiments, a sample is a prostate tissue biopsy. In some embodiments, a sample is a blood or blood plasma sample.

In some aspects, the disclosure provides a prostate antigen detection kit for quantifying levels of a prostate antigen, the kit comprising a minimal set of informative prostate antigen standards for quantifying levels of a prostate antigen in a sample using an immunoassay, in which each prostate antigen standard is present in a container as a solution. In some embodiments, a minimal set of informative prostate antigen standards comprises at least two titers containing predetermined quantities of prostate antigens, in which the largest titer of the set is between i) the blood prostate antigen concentration of the upper quartile of a target population of subjects and ii) 75-fold higher than that blood prostate antigen concentration. In some embodiments, the quantity of the smallest non-zero titer of the set is below the limit of quantification of the immunoassay. In some embodiments, a prostate antigen is selected from the group consisting of: total prostate specific antigen (tPSA), free prostate specific antigen (fPSA), intact prostate specific antigen (iPSA), and human kallikrein 2 (hK2). In some embodiments, the prostate antigen is iPSA or hK2. In some embodiments, a prostate antigen is intact prostate specific antigen (iPSA). In some embodiments, the smallest non-zero titer of the set is 0.025 ng/mL. In some embodiments, the largest titer of the set is 15 ng/mL. In some embodiments, the minimal set of informative prostate antigen standards consists of the following titers of prostate antigen standard: 0 ng/mL, 0.025 ng/mL, 0.089 ng/mL, 0.322 ng/mL, 1.157 ng/mL, 4.167 ng/mL, and 15 ng/mL. In some embodiments, a prostate antigen is hK2. In some embodiments, the smallest non-zero titer of the set is 0.002 ng/mL. In some embodiments, the largest titer of the set is 8 ng/mL. In some embodiments, a minimal set of informative prostate antigen standards consists of the following titers of prostate antigen standard: 0 ng/mL, 0.002 ng/mL, 0.011 ng/mL, 0.055 ng/mL, 0.290 ng/mL, 1.524 ng/mL, and 8 ng/mL. In some embodiments, a minimal set of informative prostate antigen standards consists of seven titers of prostate antigen standard. In some embodiments, each intermediate titer of prostate antigen standard is equidistant from the titer above and below it on a logarithmic scale.

In some aspects, the disclosure relates to a method for preparing prostate antigen standards for quantifying levels of a prostate antigen in a sample, the method comprising: (i) obtaining an antigen associated with prostate cancer; (ii) preparing a stock solution of the antigen in a suitable buffer, in which the stock solution is at a titer between i) the blood prostate antigen concentration of the upper quartile of a target population of subjects and ii) 75-fold higher than that blood prostate antigen concentration; and (iii) preparing a minimal set of prostate antigen standards by serial dilution of the stock solution, such that each intermediate titer of prostate antigen standard is equidistant from the titer above and below it on a logarithmic scale. In some embodiments, a target population of subjects consists of men, the median age of which is in a range of 60 to 70 years. In some embodiments, a target population of subjects consists of men, the lower quartile age of which is in a range of 55 to 65 years. In some embodiments, a target population of subjects consists of men, the upper quartile age of which is in a range of 65 to 75 years. In some embodiments, the prostate antigen is selected from the group consisting of: total prostate specific antigen (tPSA), free prostate specific antigen (fPSA), intact prostate specific antigen (iPSA), and human kallikrein 2 (hK2). In some embodiments, the prostate antigen is iPSA or hK2. In some embodiments, the prostate antigen is intact prostate specific antigen (iPSA). In some embodiments, the smallest non-zero titer of the set is 0.025 ng/mL. In some embodiments, the largest titer of the set is 15 ng/mL. In some embodiments, the minimal set of informative prostate antigen standards consists of the following titers of prostate antigen standard: 0 ng/mL, 0.025 ng/mL, 0.089 ng/mL, 0.322 ng/mL, 1.157 ng/mL, 4.167 ng/mL, and 15 ng/mL. In some embodiments, the prostate antigen is hK2. In some embodiments, the smallest non-zero titer of the set is 0.002 ng/mL. In some embodiments, the largest titer of the set is 8 ng/mL. In some embodiments, a minimal set of informative prostate antigen standards consists of the following titers of prostate antigen standard: 0 ng/mL, 0.002 ng/mL, 0.011 ng/mL, 0.055 ng/mL, 0.290 ng/mL, 1.524 ng/mL, and 8 ng/mL. In some embodiments, a minimal set of informative prostate antigen standards consists of seven titers of prostate antigen standard. In some embodiments, each intermediate titer of prostate antigen standard is equidistant from the titer above and below it on a logarithmic scale.

DETAILED DESCRIPTION OF DISCLOSURE

Figure 1:
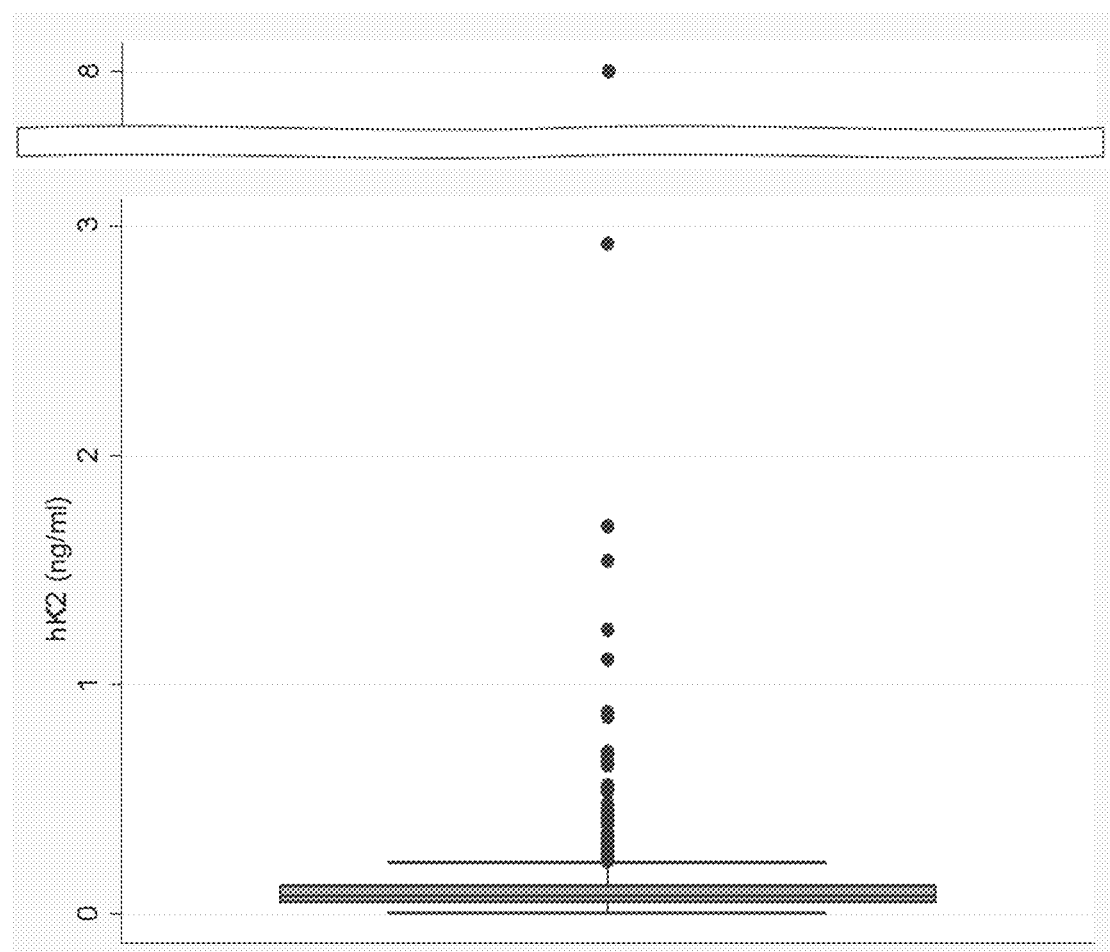
FIG. 1 shows a non-limiting box and whisker plot of hK2 levels (ng/mL) of a population of subjects (N=1012).

Aspects of the disclosure provide standards for quantifying the level of a prostate antigen in a sample. The standards described in the disclosure represent an improvement over currently used standards because they are cost effective (e.g., require a lower amount of prostate antigen) and provide sets of values that more closely aligned with clinically-relevant ranges of prostate antigens. The disclosure relates, in part, to a recognition that calibrating the titer range to a minimal set of informative prostate antigen standards significantly reduces cost while simultaneously providing increased accuracy of prostate level quantification. Thus, in some aspects, the disclosure provides improved methods for quantifying levels of a prostate antigen. The methods typically involve performing an immunoassay to detect presence of a prostate antigen in a sample and quantifying levels of the prostate antigen detected in the sample in relation to a minimal set of informative prostate antigen standards detected using the same immunoassay.

As used herein, a "minimal set of informative prostate antigen standards" is a set of prostate antigen standards for a particular immunoassay that includes at least two titers containing predetermined quantities of prostate antigens, in which the quantity of the smallest titer of the set is below the limit of quantification of the immunoassay and in which the quantity of the largest titer of the set is between i) the blood prostate antigen concentration of the upper quartile of a target population of subjects (e.g., men suspected of having prostate cancer or of being in need for a biopsy) and ii) 100-fold higher than that blood prostate antigen concentration. In some embodiments, the largest titer of the set is between i) the blood prostate antigen concentration of the upper quartile of a target population of subjects and ii) 75-fold higher than that blood prostate antigen concentration. In some embodiments, the largest titer of the set is between i) the blood prostate antigen concentration of the upper quartile of a target population of subjects and ii) 50-fold higher than that blood prostate antigen concentration. In some embodiments, the largest titer of the set is between i) the blood prostate antigen concentration of the upper quartile of a target population of subjects and ii) 25-fold higher than that blood prostate antigen concentration.

In some embodiments, the quantity of the smallest non-zero titer of the set is below the limit of quantification of the immunoassay. As used herein, the term "limit of quantification" refers to the smallest amount of material detectable and quantifiable by using the immunoassay. In some embodiments, the limit of quantification is the smallest amount of material detectable and quantifiable with a coefficient of variation of less than 25%, less than 15%, less than 5%, or less than 1% by using the immunoassay.

In some embodiments, the quantity of the smallest non-zero titer of the set is below the limit of detection of the immunoassay. As used herein, the term "limitation of detection" refers to the smallest amount of material detectable but not necessarily quantifiable by using the immunoassay.

Prostate Antigen Standards

In some aspects, the disclosure provides prostate antigen standards for quantifying the level of a prostate antigen in a sample. As used herein, a "prostate antigen standard" is a substantially homogenous preparation of a prostate antigen suitable for establishing a reference against which an unknown quantity of the prostate antigen can be measured. In some embodiments, a prostate antigen standard comprises a preparation of prostate antigen that is at least 80%, at least 85%, at least 90%, at least 95%, or at least 99% pure. However, in some embodiments, the standard comprises a homogenous preparation of prostate antigen in a medium (e.g., as a solution) similar to that of the sample to be tested (e.g., a blood, serum, urine or plasma sample). For example, the prostate antigen standard may be spiked into a blood, serum, urine or plasma sample that is otherwise free of the prostate antigen. In this way, the background of the prostate antigen standard and the unknown sample are similar or the same, which can improve accuracy of detection and quantification.

In some embodiments, concentration curves are used to determine the concentration of a particular antigen in a sample. For example, a concentration curve may be produced by plotting relative fluorescence units (RFU) versus a plurality of a known concentrations of an antigen (e.g. a set of antigen concentrations). The RFU value obtained from a sample having an unknown antigen concentration may then be compared to the concentration curve to determine the antigen concentration of the sample.

In some embodiments, the standard material comprises a set of antigen titers. As used herein, the term "set of antigens" refers to a plurality of discrete antigen titers. In some embodiments, each antigen titer of a set is housed in a different container. In some embodiments, a set of antigens standards is produced from a master stock having an antigen titer higher than the maximum antigen concentration of the set. In some embodiments, a set of antigens standards is produced from a master stock by serially diluting the stock. In some embodiments, a set of antigens is produced from a master stock having an antigen concentration at the maximum antigen concentration of the set. In some embodiments, a set of antigens is between 1 and 20 antigen titers, 5 and 15 antigen titers, or 8 and 12 antigen titers. In some embodiments, a set of antigens is 1, 2, 3, 4, 5, 6, 7, 8, 9, 10, 11, 12, 13, 14, 15, 16, 17, 18, 19, or 20 antigen titers.

In some aspects, the disclosure relates to a finding that establishing a minimal set of prostate antigen standards significantly reduces cost while simultaneously providing increased accuracy of prostate antigen level quantification. As used herein, the term "informative" refers to a characteristic of an antigen or set of antigens to provide clinically-relevant quantification of an antigen in a sample having an unknown antigen amount or concentration. For example, a standard having a broad range of antigen concentrations may produce a set of values (e.g., a concentration curve) with clinically relevant antigen concentrations falling outside the useful range of the values. This can reduce the predictive power of the values provided and thus tends to be less informative. On the other hand, use of standards having an range of antigen concentrations consistent with likely antigen amounts or concentrations in a target population is informative because the resulting values (e.g., concentration curve) have a higher number of clinically relevant antigen concentrations falling within the useful range of the values (curve).

In some aspects, the disclosure relates to the distribution of prostate antigen concentrations in a set of informative prostate antigen concentrations. In some embodiments, each informative prostate antigen concentration of a set is equidistant from the informative prostate antigen concentration above and/or below it. As used herein, the term "equidistant" refers to the number of units between prostate antigen concentrations. For example, the concentrations 1 ng/mL, 2 ng/mL, 3 ng/mL, and 4 ng/mL are each equidistant from (i.e., 1 ng/mL) the concentration above and/or below on a linear scale. The units may be measured on any appropriate scale, such as a linear scale or a logarithmic scale (e.g., $\log_{10}$, natural log (LN), etc.). In some embodiments, each informative prostate antigen concentration of a set is equidistant from the informative prostate antigen concentration above and/or below it on a logarithmic scale. For example, an informative set of iPSA antigens may be 0 ng/mL, 0.025 ng/mL, 0.089 ng/mL, 0.322 ng/mL, 1.157 ng/mL, 4.167 ng/mL, and 15 ng/mL. As another example, an informative set of hK2 antigens may be 0 ng/mL, 0.002 ng/mL, 0.011 ng/mL, 0.055 ng/mL, 0.290 ng/mL, 1.524 ng/mL, and 8 ng/mL. Equidistant concentrations of an antigen may be prepared by any suitable method, such as serial-dilution, or dissolving a quantity of antigen in an appropriate buffer to obtain a solution having an informative antigen concentration.

Various types of antigens are contemplated by the disclosure. Examples of antigens include but are not limited to peptides, proteins, lipoproteins, glycoproteins, and small molecules (e.g., haptens). Other non-limiting examples of antigens include nucleic acids, such as DNA, RNA and oligonucleotides. In some embodiments, the disclosure provides standards comprising prostate antigens. As used herein, the term "prostate antigen" refers to an antigen that is produced or expressed in the prostate of a subject. Examples of prostate antigens include but are not limited to total prostate specific antigen (tPSA), free prostate specific antigen (fPSA), intact prostate specific antigen (iPSA) and human kallikrein 2 (hK2). In some embodiments, the standard material comprises an informative set of iPSA concentrations. In some embodiments, the standard material comprises an informative set of hK2 concentrations.

As used herein, the term "subject" refers to a mammal having or suspected of having cancer, or being tested for cancer. Examples of subjects include humans, non-human primates (e.g., marmosets and monkeys), pigs, horses, cats, dogs, rats, and mice. In some embodiments, a subject is a human subject. In some embodiments, the subject is a human having or suspected of having prostate cancer. In some embodiments, the subject is a human being tested for prostate cancer. Human subjects may or may not display signs or symptoms of prostate cancer, including a need to urinate frequently, especially at night, difficulty starting urination or holding back urine, weak or interrupted flow of urine, painful or burning urination, difficulty in having an erection, painful ejaculation, and/or blood in urine or semen.

Containers for standard materials are also contemplated by the disclosure. Standard materials as described herein may be contained in any suitable vessel. Non-limiting examples of suitable vessels include vials (e.g., glass vials or plastic vials), test tubes, blister packs, bottles, pouches, and assay plates. In some embodiments, a set of antigen concentrations (e.g., a set of informative prostate antigen concentrations) may be housed in a plurality of containers. For example, a set of seven informative prostate antigen standards may be stored in seven sealed tubes, each tube housing a single informative prostate antigen standard. Generally, standard materials are in liquid phase while being contained by a container. However, the skilled artisan recognizes that a standard material, for example a protein antigen, may be contained in a powder form (for example, in a lyophilized format) and reconstituted into an informative antigen concentration with an appropriate amount of solvent (for example, water or a buffer solution).

In some embodiments, the disclosure relates to kits comprising standard materials. Kits may include a standard material, related equipment for performing an assay (e.g. assay plates, appropriate buffers, sample collection instruments and apparatus, etc.) and instructions for performing an assay using the standard material. In some embodiments, the disclosure provides a kit having a plurality of containers, each container housing a standard material. In some embodiments, each container comprises an informative prostate antigen concentration of a set of informative prostate antigen concentrations. In some embodiments, kits described herein further comprise instructions for quantifying levels of prostate antigen from a sample.

Methods of preparing prostate antigen standards are also contemplated by the disclosure. In some embodiments, the disclosure provides a method for preparing a prostate antigen standard for quantifying levels of a prostate antigen, the method comprising (i) obtaining an antigen associated with prostate cancer; (ii) preparing a stock solution of the antigen in a suitable buffer or solvent; and, (iii) preparing a set of informative concentrations from the stock solution, in which each informative concentration of the set has a concentration that is equidistant from the concentration above and/or below it on a log scale. In some embodiments, the antigen associated with prostate cancer is a prostate antigen. In some embodiments, the prostate antigen is selected from the group consisting of tPSA, fPSA, iPSA, and hK2. In some embodiments, the prostate antigen is iPSA or hK2. Non-limiting examples of suitable buffers and/or solvents include water, phosphate-buffered saline (PBS), and tris-buffered saline (TBS). A set of informative antigen concentrations from a stock solution may be prepared, for example, by serially diluting the stock solution to arrive at a plurality of informative antigen concentrations.

Assays for Quantification of Prostate Antigen Levels

In some aspects, the disclosure relates to methods for quantifying prostate antigen levels. The disclosure is based, in part, on the discovery that the prostate antigen standards described by this disclosure allow for more cost-effective and accurate quantification of prostate antigens than currently used prostate antigen standards.

Accordingly, in some aspects, the disclosure provides a method for quantifying levels of a prostate antigen, the method comprising, performing an immunoassay to detect presence of a prostate antigen in a sample and quantifying levels of the prostate antigen detected in the sample based on values derived from detection of a set of informative prostate antigen concentrations by the immunoassay. For example, in some embodiments, the informative set of antigen concentrations is an informative set of iPSA concentrations. In some embodiments, the informative set of antigen concentrations is an informative set of hK2 concentrations. Additional methods for detecting the presence of prostate antigens are disclosed, for example in U.S. Ser. No. 61/972,099, filed on Mar. 28, 2014, the content of which is incorporated herein by reference in its entirety.

Immunoassays

Levels of prostate specific antigens (e.g., tPSA, iPSA, fPSA, and hK2) can be assessed by any appropriate method. In some embodiments, antibodies or antigen-binding fragments are provided that are suited for use in immunoassays. Immunoassays utilizing such antibody or antigen-binding fragments may be competitive and non-competitive immunoassays, in either a direct or indirect format. Non-limiting examples of such immunoassays are dissociation-enhanced lanthanide fluorescence immunoassay (DELFIA®), Enzyme Linked Immunoassay (ELISA), radioimmunoassay (RIA), sandwich assay (immunometric assay), flow cytometry, western blot assay, immunoprecipitation assays, immunohistochemistry, immuno-microscopy, lateral flow immunochromatographic assays, and proteomics arrays.

In some embodiments, the immunoassay is DELFIA®. DELFIA® (dissociation-enhanced lanthanide fluorescence immunoassay) is a time-resolved fluorescence (TRF) intensity technology that is designed to detect the presence of a compound or biomolecule using lanthanide chelate labeled reagents. DELFIA® assays are flexible, compatible with a variety of plate readers, and, as a wash-based technology, are compatible with various sample types (e.g., blood, serum, plasma, cells, etc.). The technology is based on fluorescence of lanthanide chelates (Europium, Samarium, and Terbium). The fluorescence decay time of these lanthanide chelate labels is much longer than traditional fluorophores, allowing efficient use of temporal resolution for reduction of autofluorescent background. The large Stokes' shift (difference between excitation and emission wavelengths) and the narrow emission peaks contribute to increasing signal-to-noise ratio. Sensitivity is further increased because of the dissociation-enhancement principle: the lanthanide chelate is dissociated and a new highly fluorescent chelate is formed into a protective micellar solution. Unlike traditional ELISA, DELFIA® does not involve the use of an enzyme (e.g., horse radish peroxidase, HRP) to generate a detectable signal.

Antigens or antibodies or antigen-binding fragments can be immobilized, e.g., by binding to solid supports (e.g., carriers, membrane, columns, proteomics array, etc.). Examples of solid support materials include glass, polystyrene, polyvinyl chloride, polyvinylidene difluoride, polypropylene, polyethylene, polycarbonate, dextran, nylon, amyloses, natural and modified celluloses, such as nitrocellulose, polyacrylamides, agaroses, and magnetite. The nature of the support can be either fixed or suspended in a solution (e.g., beads).

In some embodiments, labeled antibodies or antigen binding fragments may be used as tracers to detect antigen bound antibody complexes. Examples of the types of labels which can be used to generate tracers include enzymes, radioisotopes, colloidal metals, fluorescent compounds, magnetic, chemiluminescent compounds, and bioluminescent compounds. Radiolabeled antibodies are prepared in known ways by coupling a radioactive isotope such as $^{153}$Eu, $^{3}$H, $^{32}$P, $^{35}$S, $^{59}$Fe, or $^{125}$I, which can then be detected by gamma counter, scintillation counter, or by autoradiography. As discussed herein, antibodies and antigen-binding fragments may alternatively be labeled with enzymes such as yeast alcohol dehydrogenase, horseradish peroxidase, alkaline phosphatase, and the like, then developed and detected spectrophotometrically or visually. Suitable fluorescent labels include fluorescein isothiocyanate, fluorescamine, rhodamine, and the like. Suitable chemiluminescent labels include luminol, imidazole, oxalate ester, luciferin, and others.

An immunoassay may comprise contacting the sample, e.g., a plasma sample, containing an antigen with an antibody, or antigen-binding fragment (e.g., F(ab), F(ab)$_2$), under conditions enabling the formation of binding complexes between antibody or antigen-binding fragment and antigen. In some embodiments, a plasma sample is contacted with an antibody or antigen-binding fragment under conditions suitable for binding of the antibody or antigen-binding fragment to a target antigen, if the antigen is present in the sample. This may be performed in a suitable reaction chamber, such as a tube, plate well, membrane bath, cell culture dish, microscope slide, and other chamber. In some embodiments, an antibody or antigen-binding fragment is immobilized on a solid support. An antibody or antigen binding fragments that binds to an antigen in a sample may be referred to as a capture antibody. In some embodiments, the capture antibody comprises a tag (e.g., a biotin label) that facilitates its immobilization to a solid support by an interaction involving the tag (e.g., a biotin-streptavidin interaction in which the streptavidin is immobilized to a solid support). In some embodiments, the solid support is the surface of a reaction chamber. In some embodiments, the solid support is of a polymeric membrane (e.g., nitrocellulose strip, Polyvinylidene Difluoride (PVDF) membrane, etc.). In other embodiments, the solid support is a biological structure (e.g., bacterial cell surface). Other exemplary solid supports are disclosed herein and will be apparent to one of ordinary skill in the art.

In some embodiments, the antibody and antigen-binding fragment is immobilized on the solid support prior to contacting with the antigen. In other embodiments, immobilization of the antibody and antigen-binding fragment is performed after formation of binding complexes. In still other embodiments, antigen is immobilized on a solid support prior to formation of binding complexes. In some embodiments, a tracer may be added to the reaction chamber to detect immobilized binding complexes. In some embodiments, the tracer comprises a detectably labeled secondary antibody directed against the antigen. In some embodiments, the tracer comprises a detectably labeled secondary antibody directed against the capture antibody. In some embodiments, the primary antibody or antigen-binding fragment is itself detectably labeled.

In one embodiment, immunoassay methods disclosed herein comprise immobilizing antibodies or antigen-binding fragments to a solid support; applying a sample (e.g., a plasma sample) to the solid support under conditions that permit binding of antigen to the antibodies or antigen-binding fragment, if present in the sample; removing the excess sample from the solid support; applying a tracer (e.g., detectably labeled antibodies or antigen-binding fragments) under conditions that permit binding of the tracer to the antigen-bound immobilized antibodies or antigen-binding fragments; washing the solid support and assaying for the presence tracer.

In some embodiments, the antibody and antigen-binding fragment is immobilized on the solid support after contacting with the antigen in a reaction chamber. In some embodiments, the antibody and antigen-binding fragment is immobilized on the solid support prior to contacting with the antigen in a reaction chamber. In either case, a tracer may be added to the reaction chamber to detect immobilized binding complexes. In some embodiments, a tracer comprises a detectably labeled secondary antibody directed against the antigen. In some embodiments, the tracer comprises a detectably labeled secondary antibody directed against the primary antibody or antigen-binding fragment. As disclosed herein, the detectable label may be, for example, a radioisotope, a fluorophore, a luminescent molecule, an enzyme, a biotin-moiety, an epitope tag, or a dye molecule. Suitable detectable labels are described herein.

In some embodiments, it has been found that performing certain immunoassays in low pH buffer leads to more sensitive antigen detection. Accordingly, in some embodiments, a tracer antibody is contacted with a capture antibody in a buffer having a pH in a range of 6.5 to less than 7.75 such that the tracer binds to the capture-antibody-antigen complex. In some embodiments, the buffer pH is about 6.5, 6.6, 6.7, 6.8, 6.9, 7.0, 7.1, 7.2, 7.3, 7.4, 7.5, or 7.6.

It should be appreciated that in any of the assays disclosed herein capture antibodies may be swapped with tracer antibodies.

In some embodiments, an immunoassay that measures the level of fPSA involves contacting fPSA present in the plasma blood sample with a capture antibody specific for fPSA under conditions in which the first capture antibody binds to fPSA, thereby producing a capture-antibody-fPSA complex; and detecting the capture-antibody-fPSA complex using a tracer. The capture antibody may be a H117 antibody. In some embodiments, the tracer comprises a 5A10 antibody or fragment thereof (e.g., a F(ab) fragment). In some embodiments, the tracer comprises an antibody or fragment thereof (e.g., a F(ab) fragment) that has at least 80%, at least 85%, at least 90%, or at least 99% amino acid sequence identity to a 5A10 antibody. In some embodiments, the tracer comprises an antibody or fragment thereof (e.g., a F(ab) fragment) that has at least 90%, at least 91%, at least 92% at least 93% at least 94% at least 95%, at least 96% at least 97% at least 98%, or at least 99% amino acid sequence identity to a 5A10 antibody.

The heavy and light chain sequences of 5A10 antibody, which may be incorporated into fragments, are shown below:

```
5A10 Heavy chain
                                              (SEQ ID NO: 1)
EVQLVESGPGILQPSQTLSLTCSFSGFSLSTTGMGVSWIRQPSGKGLEWL

AHLYWDEDKRYNPSLKSRLTISEDSSRNQVFLKITSVGPADSATYYCARK

GYYGYFDYWGQGTALTVSS

5A10 Light chain
                                              (SEQ ID NO: 2)
DIVMTQSQKFMSTSVGDRVSVTCKASQNVNTDVAWYQQKPGQSPKALIFS

TSYRSSGVPDRFTGSGSGTDFTLTITNVQSEDLAEYFCQQYSNYPLTFGA

GTKVDLN
```

In some embodiments, an immunoassay that measures the level of iPSA involves contacting iPSA present in the plasma blood sample with a capture antibody specific for free PSA, which includes iPSA and nicked PSA, under conditions in which the second capture antibody binds at least to iPSA, thereby producing a capture-antibody-iPSA complex and detecting the capture-antibody-iPSA complex using a second tracer. In some embodiments, the tracer comprises a 4D4 antibody. In some embodiments, the capture antibody is a 5A10 antibody or fragment thereof (e.g., a F(ab) fragment).

In some embodiments, an immunoassay that measures the level of tPSA involves contacting tPSA present in the plasma blood sample with a capture antibody specific for tPSA under conditions in which the third capture antibody binds to tPSA, thereby producing a capture-antibody-tPSA complex; and detecting the capture-antibody-tPSA complex using a third tracer. In some embodiments, the tracer comprises a HSO antibody. In some embodiments, the capture antibody is a H117 antibody.

In some embodiments, an immunoassay that measures the level of hK2 involves contacting PSA in the plasma blood sample with blocking antibodies specific for PSA; contacting hK2 present in the plasma blood sample with a fourth capture antibody specific for hK2 under conditions in which the fourth capture antibody binds to hK2, thereby producing a capture-antibody-hK2 complex; and detecting the capture-antibody-hK2 complex using a fourth tracer. In some embodiments, the tracer comprises a 7G1 antibody. In some embodiments, the capture antibody is a 6H10F(ab)$_2$. In some embodiments, the blocking antibodies comprise a 5H7 antibody, a 5H6 antibody, and a 2E9 antibody.

Table 1 below lists antibodies and antigen-binding fragments that may be used in the methods disclosed herein and their corresponding epitopes.

TABLE 1

Antibodies and Epitopes/Sources of Antibodies

| Antibody Name | Epitope | Reference or Source |
|---|---|---|
| F(ab)$_2$ 6H10 | | Becker et al. 2000. Sensitive and Specific Immunodetection of Human Glandular Kallikrein 2 in Serum. Clin Chem. 46(2), 198-206. |
| 2E9 | amino acids 79-93 and/or 80-91 of PSA protein (SEQ ID NO: 3) | Lilja et al. 1991. Prostate-Specific Antigen in Serum Occurs Predominantly in Complex with alpha-1-Antichymotrypsin. Clin Chem. 37(9), 1618-1625. Piironen, et al. Determination and analysis of antigenic epitopes of prostate specific antigen (PSA) and human glandular kallikrein 2 (hK2) using synthetic peptides and computer modeling. Protein Science (1998), 7: 259-269 |
| 5F7 | | Nurmikko et al. 2000. Production and Characterization of Novel Anti-Prostate-specific Antigen (PSA) Monoclonal Antibodies That Do Not Detect Internally Cleaved Lys145-Lys146 Inactive PSA. Clin Chem. 46(10): 1610-1618. |
| 5H6 | amino acids 225-237 of PSA protein (SEQ ID NO: 3) | Nurmikko et al. 2000. Supra |
| 7G1 | | Nurmikko et al. 2000. Supra |
| Fab 5A10 | amino acids 75-89, 80-94 and/or 82-39 of PSA protein (SEQ ID NO: 3) | Eriksson et al. 2000. Dual-label time-resolved immunofluorometric assay of free and total Prostate-specific Antigen Based on Recombinant Fab Fragments. Clin Chem 46(5), 658-666. Piironen et al. Supra |
| 4D4 | amino acids 130-144 of PSA protein (SEQ ID NO: 3) | U.S. Pat. No. 7,872,104 |
| H117 | | U.S. Pat. No. 5,672,480 |
| H50 | | U.S. Pat. No. 5,672,480 |
| 5A10 | amino acids 75-89, 80-94 and/or 82-39 of PSA protein (SEQ ID NO: 3) | U.S. Pat. No. 5,939,533, European Collection of Animal Cell Cultures Accession number 93091201. Piironen et al. Supra |

In some aspects, the disclosure relates to the use of immunoassays for quantifying the level of an antigen in a sample. As used herein, the term "quantification" refers to determination of antigen amount or concentration in a sample based upon a prostate antigen standard having a set of informative concentrations of the antigen. For example, the level of iPSA may be quantified by contacting a set of informative iPSA concentrations with a detectable antibody; producing a set of values (e.g., a concentration curve) based upon detectable output of each antibody-bound informative iPSA concentration; contacting a sample with unknown iPSA concentration with the detectable antibody; measuring the detectable output of the antibody-bound iPSA of the sample; and, quantifying the iPSA level of the sample based upon a comparison with the set of values produced by detection of the informative concentrations.

In some embodiments, a set of values are produced by obtaining the detectable output of antibodies. In some embodiments, detectable outputs are obtained by fluorescence readers, for example fluorescent microscopes, microplate readers and/or UV spectrophotometers. In some embodiments, fluorescence readers are connected to a computer. In some embodiments, the computer comprises software (for example, SoftMax Pro™ or Gen5 Data Analysis) for the calculation of concentration curves from detectable outputs.

Aspects of the disclosure may be implemented using a computer. For example, the amount of a prostate antigen in a sample may be determined in relation to a prostate antigen standard by obtaining immunoassay measurements of the prostate antigen in the sample and comparing those, through the use of a computer, to a prostate antigen amounts in minimal set of prostate antigen standards. For example, computer systems described by the disclosure may be used to detect the output of antibody-antigen binding or to create a standard curve using the output values obtained from a set of informative antigen concentrations. The computer system may include one or more processors and one or more computer-readable non-transitory storage media (e.g., memory and one or more non-volatile storage media). The processor(s) may control writing data to and reading data from the memory and the non-volatile storage device in any suitable manner, as the aspects of the present disclosure described herein are not limited in this respect.

To perform any of the functionality described herein, e.g., to compute prostate levels based on a minimal set of informative prostate antigens, the processor(s) may execute one or more instructions, such as program modules, stored in one or more computer-readable storage media (e.g., the memory), which may serve as non-transitory computer-readable storage media storing instructions for execution by the processor. Generally, program modules include routines, programs, objects, components, data structures, etc. that perform particular tasks or implement particular abstract data types. Embodiments may also be implemented in distributed computing environments where tasks are performed by remote processing devices that are linked through a communications network. In a distributed computing environment, program modules may be located in both local and remote computer storage media including memory storage devices. Data inputs and program commands may be received by the computer through a input interface. The input interface may comprise a keyboard, touchscreen, USB port, CD drive, DVD drive, or other input interface.

It should be appreciated that various embodiments may be formed with one or more of the above-described features. The above aspects and features may be employed in any suitable combination as the present disclosure is not limited in this respect. It should also be appreciated that the drawings illustrate various components and features which may be incorporated into various embodiments. For simplification, some of the drawings may illustrate more than one optional feature or component. However, the disclosure is not limited to the specific embodiments disclosed in the drawings. It should be recognized that the disclosure encompasses embodiments which may include only a portion of the components illustrated in any one drawing figure, and/or may also encompass embodiments combining components illustrated in multiple different drawing figures.

EXAMPLES

Example 1: Sequences for PSA and Human Kallikrein 2

PSA protein
(SEQ ID NO: 3)
IVGGWECEKHSQPWQVLVASRGRAVCGGVLVHPQWVLTAAHCIRNKSVIL

LGRHSLFHPEDTGQVFQVSHSFPHPLYDMSLLKNRFLRPGDDSSHDLMLL

RLSEPAELTDAVKVMDLPTQEPALGTTCYASGWGSIEPEEFLTPKKLQCV

DLHVISNDVCAQVHPQKVTKFMLCAGRWTGGKSTCSGDSGGPLVCNGVLQ

GITSWGSEPCALPERPSLYTKVVHYRKWIKDTIVANP hK2 protein
(SEQ ID NO: 4)
IVGGWECEKHSQPWQVAVYSHGWAHCGGVLVHPQWVLTAAHCLKKNSQVW

LGRHNLFEPEDTGQRVPVSHSFPHPLYNMSLLKHQSLRPDEDSSHDLMLL

RLSEPAKITDVVKVLGLPTQEPALGTTCYASGWGSIEPEEFLRPRSLQCV

SLHLLSNDMCARAYSEKVTEFMLCAGLWTGGKDTCGGDSGGPLVCNGVLQ

GITSWGPEPCALPEKPAVYTKVVHYRKWIKDTIAANP

Example 2: Improved Standard Materials for Detecting Prostate Antigens

Previous iPSA standards had a maximum concentration ranging from 166 to 350 ng/mL. This example describes the reformulation of iPSA standards by a serial dilution of the maximum concentration of 15 ng/mL, as shown in Table 2. The Informative Set shown below provides several benefits over the prior standard sets. First, the reduction of the maximum iPSA concentration lowers cost approximately 11- to 23-fold because less antigen is required. Second, the reduced range of the assay allows more points (e.g., values) of the calibration curve to fall within the clinically-relevant range of iPSA concentrations for diagnosis of prostate cancer. Finally, the use of seven serially-diluted concentrations (e.g., equidistant concentrations) allow specifications to be placed on the raw signal values detected from the set, which improves quality control from lot-to-lot of the standards and run-to-run of the assay.

TABLE 2

Comparison of iPSA Standard Sets (ng/mL)

| Prior Standard Set 1 | Prior Standard Set 2 | Prior Standard Set 3 | Informative Standard Set |
|---|---|---|---|
| 0 | 0 | 0 | 0 |
| 0.002 | 0.016 | 0.023 | 0.025 |
| 0.095 | 0.033 | 0.084 | 0.089 |
| 0.330 | 0.22 | 0.209 | 0.322 |
| 3.70 | 2.2 | 2.06 | 1.157 |
| 37.0 | 23.3 | 19.8 | 4.167 |
| 350 | 237 | 166 | 15 |

Human kallikrein 2 (hK2) standards were reformulated in a similar manner. Previously available hK2 standards have a maximum concentration of 13.1 ng/mL to 22.7 ng/mL, as shown in Table 3. The Informative Set shown below provides several benefits over the prior standard sets. First, the reduction of the maximum hK2 concentration lowers cost approximately 1.6- to 2.8-fold because less antigen is required. Second, the reduced range of the assay allows more points (e.g., values) of the calibration curve to fall within the clinically-relevant range of hK2 concentrations for diagnosis of prostate cancer. Finally, the use of seven serially-diluted concentrations (e.g., equidistant concentrations) allow specifications to be placed on the raw signal values detected from the set, which improves quality control from lot-to-lot of the standards and run-to-run of the assay.

TABLE 3

Comparison of hK2 Standard Sets (ng/mL)

| Prior Standard Set 1 | Prior Standard Set 2 | Informative Standard Set |
|---|---|---|
| 0 | 0 | 0 |
| 0.001 | 0.002 | 0.002 |
| 0.011 | 0.023 | 0.011 |
| 0.047 | 0.055 | 0.055 |
| 0.12 | 0.211 | 0.290 |
| 1.3 | 2.01 | 1.524 |
| 13.1 | 22.7 | 8.0 |

Example 3: Use of iPSA and hK2 Standards in the 4Kscore Assay

This example describes the use of the iPSA and hK2 standards described above in the 4Kscore test. The 4Kscore Test is a calibrated multivariate individualized risk score derived from an algorithm that includes the measurement of four kallikrein proteins associated with the prostate in a blood sample-Total Prostate Specific Antigen (tPSA), Free PSA (fPSA), Intact PSA (iPSA) and human Kallikrein 2 (hK2)-plus the following clinical information: the existence (or not) of a prior negative biopsy, patient's age, and observation (or not) of nodules upon digital rectal examination (DRE) status. The algorithm calculates the risk probability for finding high grade cancer (Gleason Score 7) if a prostate biopsy were to be performed. The test is intended to be used as an aid in the clinical decision on whether to proceed with prostate biopsy.

The concentrations of tPSA and fPSA are determined with commercial assays approved for use in human diagnostics by the FDA (Roche™ Cobas® instrument and Elecsys® assays). The concentrations of iPSA and hK2 are determined using a test developed to run on the PerkinElmer® AutoDELFIA® instrument.

Venous blood sample is collected in a $K_2$EDTA tube. The tube size must be large enough to allow the collection of approximately 7.5 mL of blood (at least 5 mL of blood). To ensure good mixing with the EDTA, the tube of blood must be inverted eight times shortly after sample collection. These quantities of blood ensure that enough plasma can be obtained. The single determination of the four kallikrein markers requires approximately 1 mL of plasma. Two milliliters (2 mL) of plasma allow the assay to be re-run, if needed.

The presence of iPSA and hK2 are detected by a sandwich (noncompetitive) immunoassay. The iPSA assay employs two distinct mouse monoclonal antibody products. The capture probe is a biotinylated, recombinant $His_6$-Cys-tagged Fab fragment of the monoclonal antibody 5A10 with specificity for fPSA (of which iPSA is a component). The tracer is a Europium-labelled monoclonal antibody 4D4, with specificity to iPSA and complexed PSA (PSA-ACT). In combination, the reagents are specific for iPSA. The hK2 assay employs five distinct mouse monoclonal antibody products. The capture probe is a biotinylated, F(ab)2 fragment of 6H10 monoclonal antibody with specificity for hK2 and tPSA. The tracer is a Europium-labelled monoclonal antibody 7G1, with specificity to hK2 and tPSA. The assay requires the use of blocker antibodies for tPSA. The sample is diluted with a cocktail of three tPSA monoclonal antibodies (clones 2E9, 5F7 and 5H6), and the tracer formulation also contains 5H6. In combination, the reagents are specific for hK2.

The assays are calibrated as follows. The iPSA assay is calibrated to the DELFIA® ProStatus™ PSA Free/Total Kit, which is in turn calibrated to the WHO 96/670 (tPSA) and 96/668 (fPSA). The ProStatus assay allows the quantitative determination of tPSA and fPSA, of which iPSA is a subset molecule. Assignment of iPSA calibration solutions is derived from the average recovery obtained for the tPSA and fPSA assays. The hK2 assay is calibrated to the DELFIA® ProStatus™ PSA Free/Total Kit, which is in turn calibrated to the WHO 96/670 (tPSA) and 96/668 (fPSA). The ProStatus assay allows the quantitative determination of tPSA and fPSA, and the tPSA component has an equimolar cross-reactivity with hK2. Assignment of hK2 calibration solutions is derived from the recovery obtained for the tPSA assay.

The signals obtained from the detection of iPSA and hK2 in the immunoassays are then compared to the signals obtained from the detection of a set of standards (e.g. the calibrator solutions) using the same iPSA and hK2 antibodies. The iPSA and hK2 assays each utilize 7 standards (e.g., calibrator solutions). Measurement of standards (e.g., calibrator solutions) is used to determine the reporting range of the assay. The reporting range is defined by the limit of quantification (LoQ) at the low end and the highest calibrator at the high end. For the iPSA and hK2 assays, the LoQ was determined using CLSI EP-17A. The reporting range of the assay is shown in Table 4 below.

TABLE 4

4Kscore Reporting Range for iPSA and hK2

|  | iPSA | hK2 |
|---|---|---|
| Assay range | 0.014-15 ng/mL | 0.022-8 ng/mL |

Figure 2:
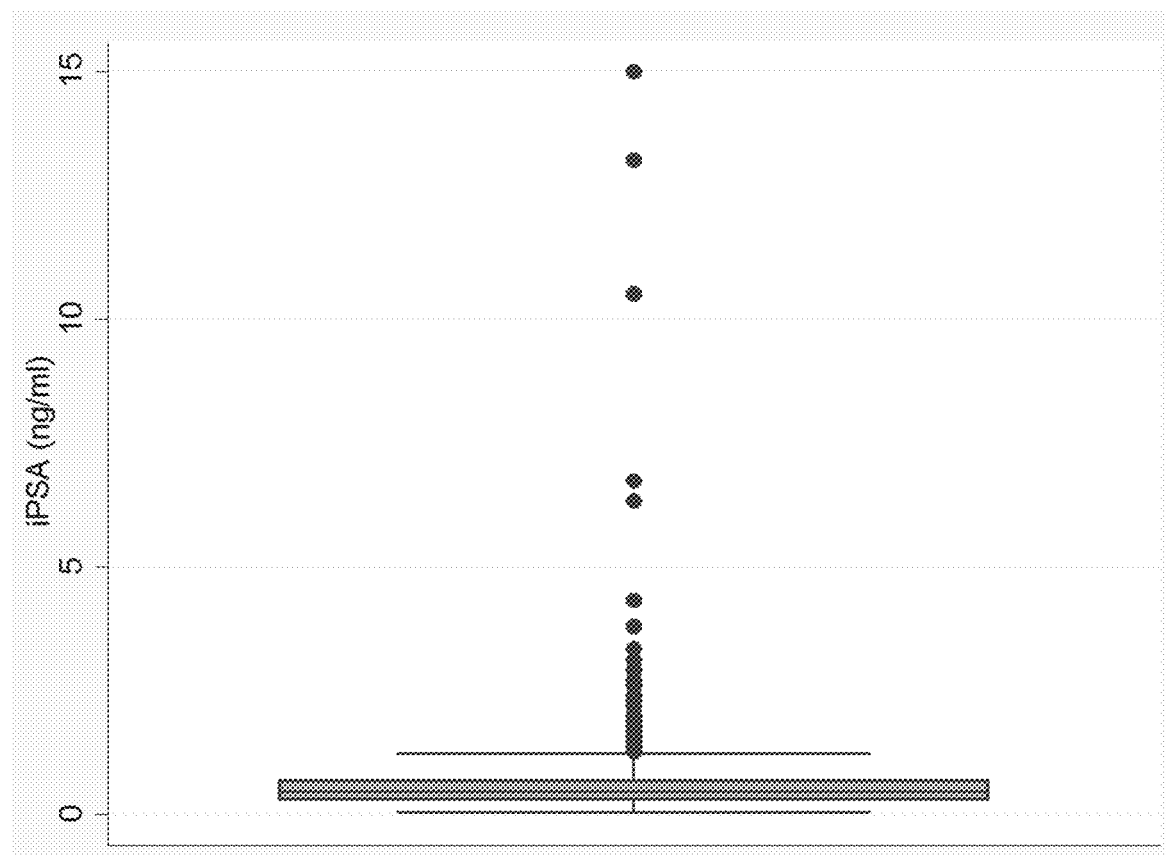
FIG. 2 shows a non-limiting box and whisker plot of iPSA levels (ng/mL) of a population of subjects (N=1012).

The expected values for iPSA and hK2 were obtained by analyzing data from the U.S. clinical trial for the 4Kscore Test, which included 1012 participants. The participants were divided into three groups based on the pathological examination of the tissues after the patient proceeded to biopsy. Data are shown below in Tables 5 and 6, and as box and whisker histograms in FIG. 1 and FIG. 2. Results indicate that 99.9% of hK2 values (1011/1012) and 99.6% of iPSA values (1008/1012) fall with the reporting range of the assays.

TABLE 5

Values of iPSA and hK2

|  |  | iPSA (ng/mL) | | hK2 (ng/mL) | |
|---|---|---|---|---|---|
|  | N | Median | Inter-quartile Range | Median | Inter-quartile Range |
| Biopsy negative | 542 | 0.416 | (0.268, 0.636) | 0.069 | (0.042, 0.107) |
| Low-grade disease (Gleason Score 6) | 239 | 0.469 | (0.311, 0.654) | 0.081 | (0.055, 0.120) |
| High grade disease (Gleason > Score 7) | 231 | 0.511 | (0.360, 0.783) | 0.107 | (0.063, 0.176) |

TABLE 6 iPSA and hk2 Percentile Data (All Subjects, N = 1012)

| percentile | hK2 (ng/mL) | iPSA (ng/mL) |
|---|---|---|
| 1 | 0.010 | 0.068 |
| 5 | 0.021 | 0.135 |
| 10 | 0.029 | 0.189 |
| 20 | 0.045 | 0.263 |
| 25 | 0.051 | 0.301 |
| 30 | 0.055 | 0.324 |
| 40 | 0.065 | 0.384 |
| 50 | 0.078 | 0.451 |
| 60 | 0.094 | 0.520 |
| 70 | 0.112 | 0.614 |
| 75 | 0.121 | 0.670 |
| 80 | 0.136 | 0.759 |
| 90 | 0.183 | 0.984 |
| 95 | 0.249 | 1.345 |
| 99 | 0.659 | 3.315 |

Assay performance for iPSA and hK2 was evaluated using CLSI EP5-A2 and CLSI EP6-A. Results are shown below in Table 7. Note that within each assay (e.g., iPSA or hK2) coefficient of variance (CV) values remain low (<15%) across the reporting range. Additionally, the $R^2$ value for each assay is 1. Together, these data indicate high accuracy and precision across the reporting range of the assay.

TABLE 7

Assay performance

|  | iPSA | hK2 |
|---|---|---|
| Precision | 0.01-0.10 ng/mL CV ≤ 15% | 0.01-0.10 ng/mL CV ≤ 10% |
|  | 0.11-1.0 ng/mL CV ≤ 8% | 0.11-1.0 ng/mL CV ≤ 8% |
|  | 1.1-15 ng/mL CV ≤ 5% | 1.1-8 ng/mL CV ≤ 10% |
| Linearity | $R^2$ = 1, slope 1.05 | $R^2$ = 1.00, slope = 1.02 |
| Accuracy by spike and recovery | 101.5% | 93.3% |
| High Dose Effect (Absence thereof) | ≥100 ng/mL | ≥90.2 ng/mL |

The clinical performance of the 4Kscore test was evaluated. A total of 1,012 patients were enrolled in a blinded, prospective clinical study at 26 urology centers in the United States. In order to obtain a cohort representative of current biopsy selection practice, enrollment was open to all men scheduled for a prostate biopsy, regardless of age, PSA, DRE, or prior biopsy. Each participant underwent a transrectal ultrasound guided prostate biopsy of at least 10 cores, and histopathologic examination was conducted according to the established practice at each center. Patients with a treatment history known to influence PSA levels were excluded. A blinded blood sample was collected prior to the biopsy and sent to OPKO Lab in Nashville, TN, for the testing of the four kallikrein markers (tPSA, fPSA, iPSA and hK2). The results of the four kallikrein markers, histopathology, age, DRE, and prior biopsy status data were unblinded and analyzed by independent biostatisticians, and are shown in Table 8. Note again that median and interquartile levels of iPSA and hK2 were within the reporting range of the assay and have a highly significant p-value.

TABLE 8

Patient Data Table

| | Negative Biopsy (N = 542; 54%) | Low Grade PCa (N = 239; 24%) | High Grade PCa (N = 231; 23%) | p-value |
|---|---|---|---|---|
| Age at Blood Draw, years | 63 (57, 68) | 64 (59, 69) | 66 (61, 72) | <0.0001 |
| <50 | 30 (5.5%) | 6 (2.5%) | 3 (1.3%) | |
| 50-75 | 481 (89%) | 220 (92%) | 197 (85%) | |
| >75 | 31 (5.7%) | 13 (5.4%) | 31 (13%) | |
| Race | | | | 0.014 |
| African American | 44 (8.1%) | 14 (5.9%) | 27 (12%) | |
| Caucasian | 458 (85%) | 218 (91%) | 193 (84%) | |
| Hispanic | 28 (5.2%) | 4 (1.7%) | 4 (1.7%) | |
| Other | 10 (1.8%) | 3 (1.3%) | 4 (1.7%) | |
| Unknown | 2 (0.4%) | 0 (0%) | 3 (1.3%) | |
| Abnormal DRE | 127 (23%) | 50 (21%) | 70 (30%) | 0.045 |
| Prior Prostate Biopsy | 139 (26%) | 38 (16%) | 22 (10%) | <0.0001 |
| Total PSA, ng/ml | 4.38 (2.88, 6.25) | 4.62 (3.60, 6.12) | 6.07 (4.37, 9.66) | <0.0001 |
| <4 | 232 (43%) | 79 (33%) | 37 (16%) | <0.0001 |
| 4-10 | 274 (51%) | 146 (61%) | 140 (61%) | |
| 10-25 | 36 (6.6%) | 11 (4.6%) | 39 (17%) | |
| >25 | 0 (0%) | 3 (1.3%) | 15 (6.5%) | |
| Free PSA, ng/ml | 0.77 (0.51, 1.20) | 0.80 (0.54, 1.15) | 0.81 (0.61, 1.27) | 0.038 |
| Free-to-Total PSA Ratio | 21 (15, 26) | 17 (13, 25) | 13 (10, 19) | <0.0001 |
| Intact PSA, pg/ml | 416 (268, 636) | 469 (311, 654) | 511 (360, 783) | <0.0001 |
| hK2, pg/ml | 69 (42, 107) | 81 (55, 120) | 107 (63, 176) | <0.0001 |
| 4Kscore | 7 (3, 15) | 14 (6, 25) | 34 (17, 66) | <0.0001 |
| <5% | 206 (38%) | 44 (18%) | 12 (5.2%) | <0.0001 |
| 5%-10% | 130 (24%) | 57 (24%) | 13 (5.6%) | |
| 10%-15% | 77 (14%) | 29 (12%) | 23 (10%) | |
| 15%-20% | 46 (8.5%) | 27 (11%) | 22 (10%) | |
| >20% | 83 (15%) | 82 (34%) | 161 (70%) | |
| Clinical T Stage | | | | |
| T1A/B | | 2 (0.8%) | 1 (0.4%) | |
| T1C | | 177 (74%) | 135 (58%) | |
| T2A | | 40 (17%) | 36 (16%) | |
| T2B | | 14 (5.9%) | 23 (10%) | |
| T2C | | 6 (2.5%) | 31 (13%) | |
| T3A | | 0 (0%) | 3 (1.3%) | |
| T4 | | 0 (0%) | 1 (0.4%) | |
| TX | | 0 (0%) | 1 (0.4%) | |
| Biopsy Gleason Grade | | | | |
| 6 | | 239 (100%) | 0 (0%) | |
| 3 + 4 | | 0 (0%) | 108 (47%) | |
| 4 + 3 | | 0 (0%) | 59 (26%) | |
| 8 | | 0 (0%) | 35 (15%) | |
| 9 | | 0 (0%) | 26 (11%) | |
| 10 | | 0 (0%) | 3 (1.3%) | |

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, e.g., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, e.g., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (e.g. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, e.g., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method comprising:
performing an immunoassay using a tracer antibody to measure a level of a prostate antigen in a sample, wherein the prostate antigen is intact prostate specific antigen (iPSA) and the tracer antibody comprises a 4D4 antibody, wherein the immunoassay comprises:
contacting iPSA present in the sample with a capture antibody specific for iPSA and nicked PSA, under conditions in which the capture antibody binds at least to iPSA, thereby producing a capture-antibody-iPSA complex;
combining the capture-antibody-iPSA complex with the 4D4 antibody in a buffer having a pH of 6.5 to 7.0 such that the 4D4 antibody specifically binds to the capture-antibody-iPSA complex; and
detecting the capture-antibody-iPSA complex bound to the 4D4 antibody;
performing the same immunoassay to measure the level of the prostate antigen in each titer in a set of prostate antigen standards, wherein the set of prostate antigen standards comprises between 3 and 15 titers containing known levels of the prostate antigen, wherein each intermediate titer of the prostate antigen is equidistant from the titer above and below it on a logarithmic scale, wherein the quantity of the smallest non-zero titer of the set is below the limit of quantification of the immunoassay, and wherein the level of the prostate antigen in the largest titer in the set is between i) a blood level of the prostate antigen in the upper quartile of a target population of male subjects and ii) a level of the prostate antigen that is 75-fold higher than the blood level in the upper quartile of the target population of male subjects; and determining the level of the prostate antigen in the sample based on the measured levels of the prostate antigen in the set of prostate antigen standards.

2. The method of claim 1, wherein the target population of male subjects consists of men, the median age of which is in a range of 60 to 70 years.

3. The method of claim 1, wherein the target population of male subjects consists of men, the lower quartile age of which is in a range of 55 to 65 years.

4. The method of claim 1, wherein the target population of male subjects consists of men, the upper quartile age of which is in a range of 65 to 75 years.

5. The method of claim 1, wherein the smallest non-zero titer of the set is 0.025 ng/mL iPSA.

6. The method of claim 5, wherein the largest titer of the set is 15 ng/mL iPSA.

7. The method of claim 1, wherein the set of prostate antigen standards consists of the following titers of iPSA: 0 ng/mL, 0.025 ng/mL, 0.089 ng/mL, 0.322 ng/mL, 1.157 ng/mL, 4.167 ng/mL, and 15 ng/mL.

8. The method of claim 1, wherein the set of prostate antigen standards consists of seven titers of the prostate antigen.

9. A prostate antigen detection kit for quantifying levels of the prostate antigen, wherein the prostate antigen is intact prostate specific antigen (iPSA), the kit comprising:
a set of prostate antigen standards for quantifying levels of the prostate antigen in a sample using an immunoassay, wherein each prostate antigen standard is present in a container as a solution, wherein the set of prostate antigen standards comprises at least two titers containing known levels of the prostate antigen, wherein each intermediate titer of the prostate antigen is equidistant from the titer above and below it on a logarithmic scale, wherein the quantity of the smallest non-zero titer of the set is below the limit of quantification of the immunoassay, and wherein the largest titer of the set is between i) a blood level of the prostate antigen in the upper quartile of a target population of male subjects and ii) a level of the prostate antigen that is 75-fold higher than the blood level in the upper quartile of the target population of male subjects;

a tracer antibody comprising a 4D4 antibody;

a buffer having a pH of 6.5 to 7.0; and instructions for quantifying levels of the prostate antigen.

10. A method comprising:

performing an immunoassay using a tracer antibody to measure a level of a prostate antigen in a sample, wherein the prostate antigen is intact prostate specific antigen (iPSA) and wherein the tracer antibody comprises a 4D4 antibody, wherein the immunoassay comprises:

contacting iPSA present in the sample with a capture antibody specific for iPSA and nicked PSA, under conditions in which the capture antibody binds at least to iPSA, thereby producing a capture-antibody-iPSA complex;

combining the capture-antibody-iPSA complex with the 4D4 antibody in a buffer having a pH of 6.5 to 7.0 such that the 4D4 antibody specifically binds to the capture-antibody-iPSA complex; and detecting the capture-antibody-iPSA complex bound to the 4D4 antibody;

performing the same immunoassay to measure the level of the prostate antigen in each titer in a set of prostate antigen standards, wherein the set of prostate antigen standards comprises between 5 and 15 titers containing known levels of the prostate antigen, wherein the level of the prostate antigen in the largest titer in the set is less than or equal to 15 ng/mL iPSA, wherein each intermediate titer of the prostate antigen is equidistant from the titer above and below it on a logarithmic scale, and wherein the quantity of the smallest non-zero titer of the set is below the limit of quantification of the immunoassay; and determining the level of the prostate antigen in the sample based on the measured levels of the prostate antigen in the set of prostate antigen standards.

11. The method of claim 10, wherein the set of prostate antigen standards consists of seven titers of the prostate antigen.

12. The method of claim 10, wherein the set of prostate antigen standards consists of the following titers of iPSA: 0 ng/mL, 0.025 ng/mL, 0.089 ng/mL, 0.322 ng/mL, 1.157 ng/mL, 4.167 ng/mL, and 15 ng/mL.

13. The method of claim 1, wherein the set of prostate antigen standards comprises between 5 and 15 titers containing known levels of the prostate antigen, and wherein the largest titer of the set is between i) the blood prostate antigen concentration of the upper quartile of a target population of subjects and ii) 25-fold higher than that blood prostate antigen concentration.

14. The method of claim 13, wherein the target population is men having a median age in a range of 60 to 70 years, in a range of 55 to 65 years, or in a range of 65 to 75 years.

15. The method of claim 1, wherein the largest titer of the set is less than or equal to 15 ng/mL iPSA.

16. The method of claim 10, wherein the smallest non-zero titer of the set is 0.025 ng/mL iPSA.

17. The method of claim 1, wherein the limit of quantification is the smallest amount of material detectable and quantifiable with a coefficient of variation of less than 25%.

18. The method of claim 10, wherein the limit of quantification is the smallest amount of material detectable and quantifiable with a coefficient of variation of less than 25%.

19. A method of determining the quantity of a prostate antigen in a sample from a subject, wherein the prostate antigen is intact prostate specific antigen (iPSA), the method comprising:

1) performing an immunoassay on the sample using a capture antibody and a tracer antibody comprising a 4D4 antibody to generate a signal for detecting the quantity of the prostate antigen in the sample, wherein the immunoassay comprises:

contacting iPSA present in the sample with a capture antibody specific for iPSA and nicked PSA, under conditions in which the capture antibody binds at least to iPSA, thereby producing a capture-antibody-iPSA complex;

combining the capture-antibody-iPSA complex with the 4D4 antibody in a buffer having a pH of 6.5 to 7.0 such that the 4D4 antibody specifically binds to the capture-antibody-iPSA complex; and detecting the capture-antibody-iPSA complex bound to the 4D4 antibody;

2) performing the immunoassay on a set of prostate antigen standards using the same capture antibody and tracer antibody to generate a set of signals, wherein each intermediate standard of the set of prostate antigen standards is equidistant from standard above and below it on a logarithmic scale, wherein the quantity of the smallest non-zero standard of the set of prostate antigen standards is below the limit of quantification of the immunoassay, and wherein the largest standard of the set of prostate antigen standards is less than or equal to 15 ng/mL iPSA; and 3) comparing the signal obtained in the sample to the set of signals to determine the quantity of prostate antigen in the sample.

20. The method of claim 19, further comprising collecting between 5 to 7.5 mLs of blood from the subject and obtaining up to 2 mLs of plasma from the blood prior to steps 1)-3), wherein the sample is the obtained plasma.

21. The method of claim 19, wherein the limit of quantification is the smallest amount of material detectable and quantifiable with a coefficient of variation of less than 25%.

22. The method of claim 19, wherein the capture antibody comprises a 5A10 antibody or fragment thereof.

23. The method of claim 19, wherein the smallest non-zero standard of the set of prostate antigen standards is 0.025 ng/mL iPSA.

24. The method of claim 19, wherein the set of prostate antigen standards comprises 0 ng/mL, 0.025 ng/mL, 0.089 ng/mL, 0.322 ng/mL, 1.157 ng/mL, 4.167 ng/mL and 15 ng/mL iPSA.

25. The method of claim 19, wherein the method further comprises determining the quantity of a second prostate antigen in the sample from the subject, wherein the second prostate antigen is human kallikrein 2 (hK2), and the method comprises:

1) Performing a second immunoassay on the sample using a second capture antibody, a second tracer antibody, and/or second blocker antibodies to generate a second signal for detecting the quantity of the second prostate antigen in the sample;

2) performing the second immunoassay on a second set of prostate antigen standards using the second capture antibody, second tracer antibody, and/or second blocker antibodies to generate a second set of signals, wherein each intermediate standard of the second set of prostate antigen standards is equidistant from the standard above and below it on a logarithmic scale, wherein the quantity of the smallest non-zero standard of the second set of prostate antigen standards is below the limit of quantification of the second immunoassay, and wherein the largest standard of the second set of prostate antigen standards is less than or equal to 8 ng/mL hK2; and 3) comparing the second signal obtained in the sample to the second set of signals to determine the quantity of second prostate antigen in the sample.

26. The method of claim 25, wherein the second tracer antibody comprises a 7G1 antibody.

27. The method of claim 25, wherein the second capture antibody comprises a 6H10 antibody or fragment thereof.

28. The method of claim 25, wherein the second blocker antibodies comprise a 5F7 antibody, a 5H6 antibody, and a 2E9 antibody.

29. The method of claim 25, wherein the smallest non-zero standard of the second set of prostate antigen standards is 0.002 ng/mL hK2.

30. The method of claim 25, wherein the second set of prostate antigen standards comprises 0 ng/mL, 0.002 ng/mL, 0.011 ng/mL, 0.055 ng/mL, 0.290 ng/mL, 1.524 ng/mL and 8 ng/mL hK2.

31. The method of claim 1, the method further comprising performing a second immunoassay to measure a level of a second prostate antigen in the sample, wherein the second prostate antigen is human kallikrein 2 (hK2);
performing the second immunoassay to measure the level of the second prostate antigen in each titer in a second set of prostate antigen standards, wherein the second set of prostate antigen standards comprises between 3 and 15 titers containing known levels of the second prostate antigen, wherein each intermediate titer of the second set of prostate antigen standards is equidistant from the titer above and below it on a logarithmic scale, wherein the quantity of the smallest non-zero titer of the second set is below the limit of quantification of the second immunoassay, and wherein the level of the second prostate antigen in the largest titer in the second set is between i) a blood level of the second prostate antigen in the upper quartile of the target population of male subjects and ii) a level of the second prostate antigen that is 75-fold higher than the blood level in the upper quartile of the target population of male subjects; and
determining the level of the second prostate antigen in the sample based on the measured levels of the second prostate antigen in the second set of prostate antigen standards.

32. The method of claim 10, wherein the method further comprises:
performing a second immunoassay to measure a level of a second prostate antigen in the sample, wherein the second prostate antigen is human kallikrein 2 (hK2);
performing the second immunoassay to measure the level of the second prostate antigen in each titer in a second set of prostate antigen standards, wherein the second set of prostate antigen standards comprises between 5 and 15 titers containing known levels of the second prostate antigen, wherein the level of the second prostate antigen in the largest titer in the second set is less than or equal to 8 ng/mL hK2, wherein each intermediate titer of the second set of prostate antigen standards is equidistant from the titer above and below it on a logarithmic scale, and wherein the quantity of the smallest non-zero titer of the second set is below the limit of quantification of the second immunoassay; and
determining the level of the second prostate antigen in the sample based on the measured levels of the second prostate antigen in the second set of prostate antigen standards.

33. The method of claim 31, wherein the largest titer of the second set is less than or equal to 8 ng/mL hK2 and/or the smallest non-zero titer of the second set is 0.002 ng/mL hK2.

34. The method of claim 31, wherein the second set of prostate antigen standards consists of the following titers of hK2: 0 ng/mL, 0.002 ng/mL, 0.011 ng/mL, 0.055 ng/mL, 0.290 ng/mL, 1.524 ng/mL, and 8 ng/mL.

35. The method of claim 32, wherein the smallest non-zero titer of the second set is 0.002 ng/mL hK2.

36. The method of claim 32, wherein the second set of prostate antigen standards consists of the following titers of hK2: 0 ng/mL, 0.002 ng/mL, 0.011 ng/mL, 0.055 ng/mL, 0.290 ng/mL, 1.524 ng/mL, and 8 ng/mL.

\* \* \* \* \*

UNITED STATES PATENT AND TRADEMARK OFFICE
CERTIFICATE OF CORRECTION

| | |
|---|---|
| PATENT NO. | : 11,921,115 B2 |
| APPLICATION NO. | : 15/081331 |
| DATED | : March 5, 2024 |
| INVENTOR(S) | : Vincent Linder et al. |

It is certified that error appears in the above-identified patent and that said Letters Patent is hereby corrected as shown below:

In the Claims

At Column 26, Line 32:
"standards is equidistant from standard above and below"
Should read:
--standards is equidistant from the standard above and below--

Signed and Sealed this
Fourteenth Day of May, 2024

Katherine Kelly Vidal
*Director of the United States Patent and Trademark Office*

SEQUENCE LISTING

```
<160> NUMBER OF SEQ ID NOS: 4

<210> SEQ ID NO 1
<211> LENGTH: 119
<212> TYPE: PRT
<213> ORGANISM: Artificial Sequence
<220> FEATURE:
<223> OTHER INFORMATION: Synthetic Polypeptide

<400> SEQUENCE: 1

Glu Val Gln Leu Val Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Thr
            20                  25                  30

Gly Met Gly Val Ser Trp Ile Arg Gln Pro Ser Gly Lys Gly Leu Glu
        35                  40                  45

Trp Leu Ala His Leu Tyr Trp Asp Glu Asp Lys Arg Tyr Asn Pro Ser
    50                  55                  60

Leu Lys Ser Arg Leu Thr Ile Ser Glu Asp Ser Ser Arg Asn Gln Val
65                  70                  75                  80

Phe Leu Lys Ile Thr Ser Val Gly Pro Ala Asp Ser Ala Thr Tyr Tyr
                85                  90                  95

Cys Ala Arg Lys Gly Tyr Tyr Gly Tyr Phe Asp Tyr Trp Gly Gln Gly
            100                 105                 110

Thr Ala Leu Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 2

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Asn Thr Asp
            20                  25                  30

Val Ala Trp Tyr Gln Gln Lys Pro Gly Gln Ser Pro Lys Ala Leu Ile
        35                  40                  45

Phe Ser Thr Ser Tyr Arg Ser Ser Gly Val Pro Asp Arg Phe Thr Gly
```

```
                    50                  55                  60
Ser Gly Ser Gly Thr Asp Phe Thr Leu Thr Ile Thr Asn Val Gln Ser
 65                  70                  75                  80

Glu Asp Leu Ala Glu Tyr Phe Cys Gln Gln Tyr Ser Asn Tyr Pro Leu
                     85                  90                  95

Thr Phe Gly Ala Gly Thr Lys Val Asp Leu Asn
                100                 105

<210> SEQ ID NO 3
<211> LENGTH: 237
<212> TYPE: PRT
<213> ORGANISM: Homo sapiens

<400> SEQUENCE: 3

Ile Val Gly Gly Trp Glu Cys Glu Lys His Ser Gln Pro Trp Gln Val
  1               5                  10                  15

Leu Val Ala Ser Arg Gly Arg Ala Val Cys Gly Gly Val Leu Val His
                 20                  25                  30

Pro Gln Trp Val Leu Thr Ala Ala His Cys Ile Arg Asn Lys Ser Val
             35                  40                  45

Ile Leu Leu Gly Arg His Ser Leu Phe His Pro Glu Asp Thr Gly Gln
 50                  55                  60

Val Phe Gln Val Ser His Ser Phe Pro His Pro Leu Tyr Asp Met Ser
 65                  70                  75                  80

Leu Leu Lys Asn Arg Phe Leu Arg Pro Gly Asp Asp Ser Ser His Asp
                 85                  90                  95

Leu Met Leu Leu Arg Leu Ser Glu Pro Ala Glu Leu Thr Asp Ala Val
            100                 105                 110

Lys Val Met Asp Leu Pro Thr Gln Glu Pro Ala Leu Gly Thr Thr Cys
        115                 120                 125

Tyr Ala Ser Gly Trp Gly Ser Ile Glu Pro Glu Glu Phe Leu Thr Pro
    130                 135                 140

Lys Lys Leu Gln Cys Val Asp Leu His Val Ile Ser Asn Asp Val Cys
145                 150                 155                 160

Ala Gln Val His Pro Gln Lys Val Thr Lys Phe Met Leu Cys Ala Gly
                165                 170                 175

Arg Trp Thr Gly Gly Lys Ser Thr Cys Ser Gly Asp Ser Gly Gly Pro
            180                 185                 190

Leu Val Cys Asn Gly Val Leu Gln Gly Ile Thr Ser Trp Gly Ser Glu
        195                 200                 205

Pro Cys Ala Leu Pro Glu Arg Pro Ser Leu Tyr Thr Lys Val Val His
    210                 215                 220

Tyr Arg Lys Trp Ile Lys Asp Thr Ile Val Ala Asn Pro
225                 230                 235

<210> SEQ ID NO 4
<211> LENGTH: 237
<212> TYPE: PRT
<213> ORGANISM: Homo sapiens

<400> SEQUENCE: 4

Ile Val Gly Gly Trp Glu Cys Glu Lys His Ser Gln Pro Trp Gln Val
  1               5                  10                  15

Ala Val Tyr Ser His Gly Trp Ala His Cys Gly Gly Val Leu Val His
                 20                  25                  30

Pro Gln Trp Val Leu Thr Ala Ala His Cys Leu Lys Lys Asn Ser Gln
```

-continued

```
                35                  40                  45
Val Trp Leu Gly Arg His Asn Leu Phe Glu Pro Glu Asp Thr Gly Gln
    50                  55                  60

Arg Val Pro Val Ser His Ser Phe Pro His Pro Leu Tyr Asn Met Ser
65                  70                  75                  80

Leu Leu Lys His Gln Ser Leu Arg Pro Asp Glu Asp Ser Ser His Asp
                85                  90                  95

Leu Met Leu Leu Arg Leu Ser Glu Pro Ala Lys Ile Thr Asp Val Val
                100                 105                 110

Lys Val Leu Gly Leu Pro Thr Gln Glu Pro Ala Leu Gly Thr Thr Cys
                115                 120                 125

Tyr Ala Ser Gly Trp Gly Ser Ile Glu Pro Glu Glu Phe Leu Arg Pro
                130                 135                 140

Arg Ser Leu Gln Cys Val Ser Leu His Leu Leu Ser Asn Asp Met Cys
145                 150                 155                 160

Ala Arg Ala Tyr Ser Glu Lys Val Thr Glu Phe Met Leu Cys Ala Gly
                165                 170                 175

Leu Trp Thr Gly Gly Lys Asp Thr Cys Gly Gly Asp Ser Gly Gly Pro
                180                 185                 190

Leu Val Cys Asn Gly Val Leu Gln Gly Ile Thr Ser Trp Gly Pro Glu
                195                 200                 205

Pro Cys Ala Leu Pro Glu Lys Pro Ala Val Tyr Thr Lys Val Val His
210                 215                 220

Tyr Arg Lys Trp Ile Lys Asp Thr Ile Ala Ala Asn Pro
225                 230                 235
```